United States Patent
Sato et al.

(10) Patent No.: US 10,201,680 B2
(45) Date of Patent: Feb. 12, 2019

(54) CATHETER

(71) Applicant: TERUMO KABUSHIKI KAISHA, Shibuya-ku, Tokyo (JP)

(72) Inventors: Yukiko Sato, Shizuoka (JP); Kazuya Omata, Shizuoka (JP); Kazuki Miyagi, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 259 days.

(21) Appl. No.: 15/085,396

(22) Filed: Mar. 30, 2016

(65) Prior Publication Data

US 2016/0250442 A1    Sep. 1, 2016

Related U.S. Application Data

(63) Continuation of application No. PCT/JP2014/075091, filed on Sep. 22, 2014.

(30) Foreign Application Priority Data

Sep. 30, 2013    (JP) .................................. 2013-205366

(51) Int. Cl.
*A61M 25/00*    (2006.01)
*A61M 25/04*    (2006.01)

(52) U.S. Cl.
CPC ...... *A61M 25/0017* (2013.01); *A61M 25/005* (2013.01); *A61M 25/0053* (2013.01);
(Continued)

(58) Field of Classification Search
CPC .......... A61M 25/0053; A61M 25/0012; A61M 25/0045; A61M 25/0054; A61M 2025/0046
See application file for complete search history.

(56) References Cited

U.S. PATENT DOCUMENTS 6,511,462 B1    1/2003    Itou et al.
2002/0022825 A1    2/2002    Saitou et al.

FOREIGN PATENT DOCUMENTS

EP    2 810 680 A1    12/2014
JP    2001-087389 A    4/2001
(Continued)

OTHER PUBLICATIONS

International Search Report (PCT/ISA/210) dated Dec. 9, 2014, by the Japanese Patent Office as the International Searching Authority for International Application No. PCT/JP2014/075091.
(Continued)

*Primary Examiner* — Scott Medway
(74) *Attorney, Agent, or Firm* — Buchanan Ingersoll & Rooney PC

(57) ABSTRACT

A catheter is configured to be introduced into and indwelled in a body lumen. The catheter includes a lumen and a deformable region that extends parallel to the lumen of the catheter in an axial direction. The catheter is bendable. The deformable region is configured to be located on an inner side of a curved section when the catheter is bent. At least a portion of an outer surface of the catheter is covered with a surface lubricating layer. A less lubricious portion is on the outer surface of the catheter at the deformable region. The less lubricious portion is less lubricious than the surface lubricating layer, and the surface lubricating layer and the less lubricious portion are disposed at the same position in the axial direction of the catheter.

13 Claims, 10 Drawing Sheets

(52) U.S. Cl.
CPC ........ *A61M 25/0054* (2013.01); *A61M 25/04* (2013.01); *A61M 2025/0046* (2013.01)

(56) References Cited

FOREIGN PATENT DOCUMENTS

| | | |
|---|---|---|
| JP | 2001-218851 A | 8/2001 |
| JP | 2002-017860 A | 1/2002 |
| JP | 2008-183226 A | 8/2008 |
| JP | 2012-513249 A | 6/2012 |
| JP | 2013-090716 A | 5/2013 |
| JP | 2013-192717 A | 9/2013 |
| WO | WO 2010/075245 A2 | 7/2010 |
| WO | 2013/115330 A1 | 8/2013 |

OTHER PUBLICATIONS

Written Opinion (PCT/ISA/237) dated Dec. 9, 2014, by the Japanese Patent Office as the International Searching Authority for International Application No. PCT/JP2014/075091.
Office Action (Notification of Reasons for Refusal) dated Apr. 3, 2018, by the Japanese Patent Office in corresponding Japanese Patent Application No. 2015-539205, and an English Translation of the Office Action. (6 pages).

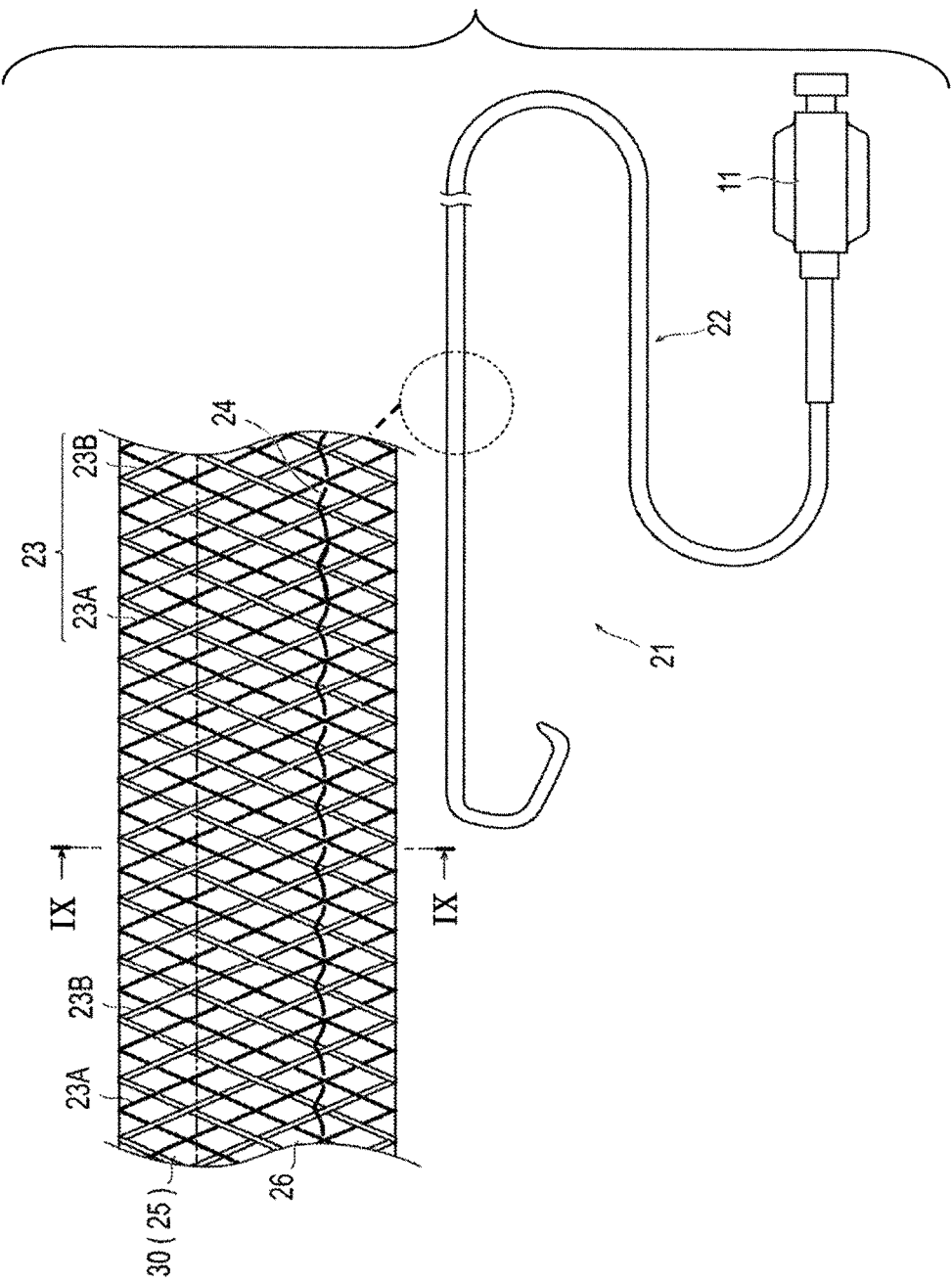

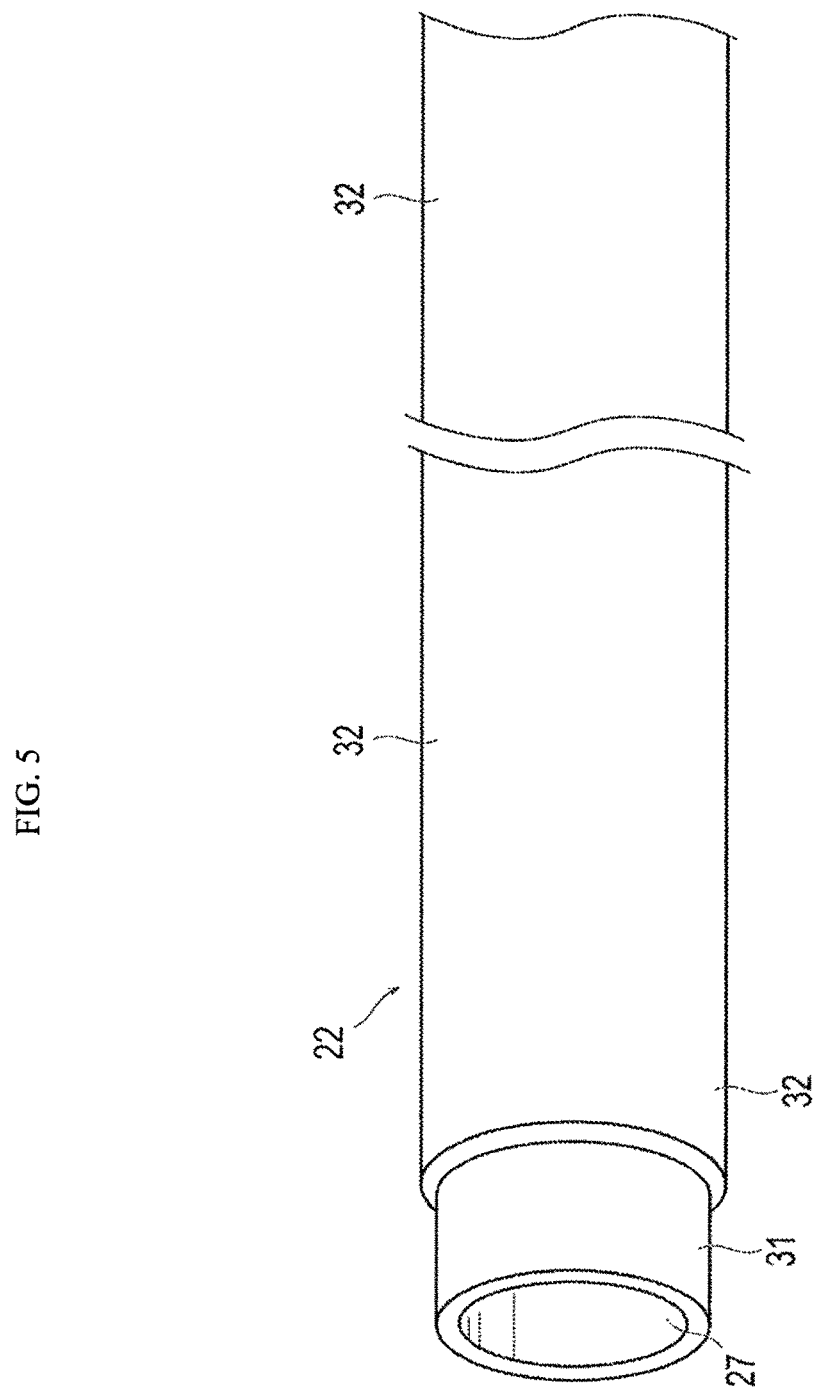

CATHETER

CROSS-REFERENCES TO RELATED APPLICATIONS

This application is a continuation of International Application No. PCT/JP2014/075091 filed on Sep. 22, 2014 and claims priority to Japanese Patent Application No. 2013-205366 filed on Sep. 30, 2013, the entire content of both of which is incorporated herein by reference.

TECHNICAL FIELD

The present invention relates to a catheter, and particularly relates to a catheter which is excellent in operability and is configured to indwell in a body lumen.

BACKGROUND DISCUSSION

In recent years, vascular lesions have been treated by actively using a catheter because the surgical invasion is very small. In the manual operation of using a catheter for treatment, the catheter is delivered to the vicinity of a target area to perform diagnosis or treatment on the target area. Therefore, the catheter needs to have excellent operability (i.e., be easily maneuverable by an operator) so that the catheter can be quickly, reliably, and selectively inserted into a vascular system which has narrow and complicated patterns. The catheter also needs to have excellent indwelling ability so that the catheter can be fixed (i.e., held securely in place) in the vicinity of the target area when the diagnosis or the treatment is performed. In addition, the catheter needs to offer a wide choice of catheter inserting portions, to reduce a diameter of the catheter to reduce the burden on a patient, facilitate and improve operability for inserting the catheter or the like, and particularly to minimize an outer diameter of the catheter as much as possible while maintaining a constant inner diameter.

For example, a micro-catheter is used to perform the diagnosis or the treatment on the target area by administering or injecting various therapeutic drugs, contrast agents, or the like used in vascular embolization, or the micro-catheter is used to perform embolization on the target area by filling a blood vessel with an embolus material. The micro-catheter has to be selectively introduced into the target area while being moved forward inside a peripheral blood vessel which has many bifurcated portions, which meanders in a complicated manner, and whose diameter is narrow, such as approximately 3 mm or smaller. Therefore, it is desirable to use a micro-catheter having operability which enables the micro-catheter to be inserted into the narrow blood vessel, and having the indwelling ability which enables the micro-catheter to be fixed to an arrangement position in the vicinity of the target area when the contrast agent or the like is used in the vicinity of the target area.

For example, the catheter disclosed in Japanese Patent Application Publication No. JP-A-2001-218851 (corresponding to US 2002/0022825 A1) includes a coil having a reinforcing effect embedded into a wall of a flexible and tubular catheter main body. According to the catheter disclosed in Japanese Patent Application Publication No. JP-A-2001-218851 described above, in order to improve the operability for inserting the catheter, an outer surface of the catheter main body is covered with a hydrophilic polymer material for lubricating the outer surface (e.g., see Paragraphs [0077] to [0081]). According to the catheter disclosed in Japanese Patent Application Publication No. JP-A-2001-218851, the outer surface is covered with this hydrophilic polymer material. Therefore, the catheter can be smoothly inserted into the target area inside an abdominal organ (for example, a liver) or the like, even if the catheter is inserted into the peripheral blood vessel which has many bifurcated portions, which meanders in a complicated manner, and whose diameter is narrow, such as approximately 3 mm or smaller.

SUMMARY

If the catheter disclosed in Japanese Patent Application Publication No. JP-A-2001-218851 is intended to indwell the blood vessel in order to administer or inject various therapeutic drugs, embolus materials, contrast agents, or the like into the target area, the frictional force against a vascular wall is weak. Consequently, there is a problem in that the catheter is less likely to be fixed to a vascular inner wall (i.e., it is likely the catheter is not secured/held in place).

The catheter disclosed here is designed in view of the above-described circumstances. The disclosed catheter has operability when the catheter is inserted into a desired area, and has improved indwelling ability in the desired area (which can achieve satisfactory backup capability).

Another object of the disclosure here is to provide a very safe catheter.

The present inventors have extensively studied in order to address the above-described problem. As a result, the present inventors found that the above-described problem can be addressed by the catheter disclosed here. The catheter includes a deformable region configured to be located on an inner side when the catheter is bent, and a less lubricious portion on an outer surface of the deformable region.

The catheter has a lumen and the catheter is able to be introduced into and indwelled in a body lumen. The deformable region of the catheter is parallel to the lumen of the catheter, which extends in an axial direction. The deformable region is configured to be located on an inner side of a curved section when the catheter is bent so as to form the curved section. At least a portion of an outer surface of the catheter is covered with a surface lubricating layer. On the outer surface of the catheter, a less lubricious portion which is less lubricious than the surface lubricating layer is disposed in at least a portion of the deformable region. The surface lubricating layer and the less lubricious portion are disposed at the same position in the axial direction of the catheter.

The catheter disclosed here is configured to be introduced into and indwelled in a body lumen of a living body. The catheter includes a lumen that extends in an axial direction and a deformable region that is parallel to the lumen of the catheter. The deformable region is configured to be located on an inner side of a curved section when the catheter is bent so as to form the curved section. At least a portion of an outer surface of the catheter is covered with a surface lubricating layer. On the outer surface of the catheter, a less lubricious portion which is less lubricious (i.e., less lubricative) than the surface lubricating layer (which will be simply referred to as the "less lubricious portion" in the present description) is disposed in at least a portion of the deformable region, and the surface lubricating layer and the less lubricious portion are disposed at the same position in the axial direction of the catheter. The less lubricious portion is arranged on the outer surface of the catheter in a position located on the inner side of bending when the catheter is bent. In addition, the surface lubricating layer is disposed on the outer surface on a side opposite to the deformable region with respect to the axis of the lumen of the catheter, and the surface lubricating portion and the less lubricious portion are arranged at the same position in the axial direction of the outer surface of the catheter. According to the catheter having the above-described configuration, satisfactory operability when the catheter is introduced into a body lumen is compatible with excellent backup capability when the catheter is caused to indwell the body lumen. Therefore, it is possible to smoothly introduce the catheter into a desired area and to reliably hold the catheter therein by using the catheter according to the present invention. Here, it is preferable that the deformable region is a region which is relatively less likely to stretch or a region which is relatively likely to contract in a circumferential direction of the catheter.

It is preferable that the catheter generally has lubricity, which enables the catheter to be smoothly introduced into the desired area, and has retention/backup capability, which enables the catheter to be firmly held (to indwell) in the desired area. On the other hand, the known catheter described in Japanese Patent Application Publication No. JP-A-2001-218851 includes a hydrophilic polymer material covering on the surface other than a proximal portion. Therefore, the known catheter can be smoothly introduced into the desired area with improved operability. However, when the known catheter is held and caused to indwell the desired area in order to administer and inject a therapeutic drug or a contrast agent, satisfactory backup force (i.e., retaining force) cannot be expected due to low friction on a wall of a body lumen (for example, a blood vessel).

In contrast, the deformable region of the catheter disclosed here is located on the inner side of the curved section when the catheter is bent, and the surface lubricating portion and the less lubricious portion are installed at the same position eccentric to a central axis (axis) of the lumen of the catheter. Therefore, the presence of the surface lubricating portion enables the catheter to be smoothly inserted (introduced) into a position inside a predetermined body lumen (for example, the blood vessel). On the other hand, in a case where a distal end of the catheter is introduced into the predetermined position, the less lubricious portion which is present at the same position in the axial direction as the position where the surface lubricating portion is present can be brought into contact with the body lumen wall. In this case, surface lubricity of the less lubricious portion is low. Accordingly, strong friction force (that is, excellent retention or backup capability) between the catheter and the body lumen wall at the contact portion enables the catheter to be effectively held at the unchanged position. Therefore, it is possible for the disclosed catheter to improve indwelling convenience (retention or backup capability) at a desired position while satisfactorily maintaining operability when the catheter is introduced into the desired position.

The deformable region of the catheter is configured to be located on the inner side when the catheter is bent. Accordingly, when the catheter is moved forward inside the bent body lumen or the like, the outer surface of the deformable region does not come into contact with the body lumen wall. Therefore, the less lubricious portion disposed in the deformable region does not come into contact with the body lumen wall, and the less lubricious portion does not interfere with the movement of the catheter when the catheter is moved forward inside the bent body lumen or the like. In addition, the outer surface of the catheter located on the side opposite to the deformable region having the less lubricious portion with respect to the axis of the lumen of the catheter is covered with the surface lubricating layer. In this manner, when the catheter is moved forward inside the bent body lumen or the like, a portion having the surface lubricating layer on the outer surface of the catheter always comes into contact with the body lumen wall. Accordingly, it is possible to achieve improved operability of the catheter. In addition, in a case where the catheter is intended to be fixed at a predetermined position, the catheter is slightly pulled back (i.e., moved proximally) towards an operating hand side so as to unbend the catheter inside the body lumen. In this manner, the catheter is allowed to pass through the inside of the bent body lumen wall, and the outer surface of the deformable region of the catheter comes into contact with the body lumen wall. In this manner, the inside of the bent body lumen wall and the less lubricious portion of the outer surface of the catheter come into contact with each other. Accordingly, it is possible to easily fix the catheter inside the body lumen. Here, unbending the catheter inside the body lumen means shortening the length of the catheter inserted into the body lumen by pulling back the catheter to the operating hand side so that the catheter in a state illustrated in FIG. 3A is brought into a state illustrated in FIG. 3C, for example.

BRIEF DESCRIPTION OF DRAWINGS

In FIG. 1, a portion is transparent so that a reinforcement member and a wire member embedded in the main body of the catheter are visible. In FIG. 1, the reference numeral 1 represents the catheter; the reference numeral 2 represents a catheter main body; the reference numeral 3 represents the reinforcement member; the reference numeral 4 represents the wire member; the reference numeral 5 represents a less lubricious portion; the reference numeral 6 represents a surface lubricating portion; the reference numeral 7 represents a lumen; the reference numeral 9 represents a guide wire member; the reference numeral 10 represents a deformable region; and the reference numeral 11 represents a hub.

In FIG. 2, the reference numeral 4 represents the wire member; the reference numeral 5 represents the less lubricious portion; the reference numeral 6 represents the surface lubricating portion; and the reference numeral 8 represents an axis.

FIG. 3B is a schematic sectional view taken along line III B-III B of the catheter illustrated in FIG. 3A. FIG. 3D is a schematic sectional view taken along line III D-III D of the catheter illustrated in FIG. 3C. In FIGS. 3A-3D, a portion is transparent so that the reinforcement member and the wire member embedded in the main body of the catheter are visible. In FIGS. 3A-3D, the reference numeral 1 represents the catheter; the reference numeral 3 represents the reinforcement member; the reference numeral 4 represents the wire member; the reference numeral 7 represents the lumen; the reference numeral 10 represents the deformable portion; the reference numeral 41 represents a blood vessel; the reference numeral 42 represents a vascular inner wall on an outer side of a vascular bent section; and the reference numeral 43 represents a vascular inner wall on an inner side of the vascular bent section.

FIG. 4 is a plan view and a partially enlarged view illustrating an overall configuration example of a catheter according to another embodiment (second embodiment) of the present invention. In FIG. 4, the reference numeral 21 represents the catheter; the reference numeral 22 represents a catheter main body; the reference numeral 23 represents a reinforcement member; the reference numeral 23A represents a first reinforcement member; reference numeral 23B represents a second reinforcement member; the reference numeral 25 represents a less lubricious portion; the reference numeral 26 represents a surface lubricating portion; the reference numeral 30 represents a deformable region; and the reference numeral 11 represents a hub.

FIG. 5 is an explanatory view schematically illustrating a structural example of the catheter illustrated in FIG. 4. In FIG. 5, the reference numeral 22 represents the catheter main body; the reference numeral 27 represents a lumen; the reference numeral 31 represents a substrate tube (inner layer); and the reference numeral 32 represents an intermediate layer.

In FIG. 6, the reference numeral 22 represents the catheter main body; the reference numeral 27 represents the lumen; the reference numeral 31 represents the substrate tube (inner tube); the reference numeral 32 represents the intermediate layer; and the reference numeral 33 represents an outer layer.

In FIGS. 7A and 7B, the reference numeral 23 represents the reinforcement member; the reference numeral 23A represents the first reinforcement member; and the reference numeral 23B represents the second reinforcement member.

FIG. 8B is a schematic sectional view taken along line VIII B-VIII B of the catheter illustrated in FIG. 8A. FIG. 8D is a schematic sectional view taken along line VIII D-VIII D of the catheter illustrated in FIG. 8C. In FIGS. 8A-8D, a portion is transparent so that the reinforcement member and the wire member embedded in the main body of the catheter are visible. In FIGS. 8A-8D, the reference numeral 7 represents the lumen; the reference numeral 21 represents the catheter; the reference numeral 23 represents the reinforcement member; the reference numeral 24 represents a wire member; the reference numeral 30 represents the deformable region; the reference numeral 41 represents the blood vessel; the reference numeral 42 represents the vascular inner wall on the outer side of the vascular bent section; and the reference numeral 43 represents the vascular inner wall on the inner side of the vascular bent section.

In FIG. 9, the reference numeral 24 represents the wire member; the reference numeral 25 represents the less lubricious portion; the reference numeral 26 represents the surface lubricating portion; and the reference numeral 28 represents an axis.

In FIG. 10, the reference numeral 50 represents a friction measuring instrument; the reference numeral 51 represents a glass laboratory dish; the reference numeral 52 represents a rubber terminal; the reference numeral 53 represents a weight; and the reference numeral 54 represents a sample.

DESCRIPTION OF EMBODIMENTS

Figure 1:
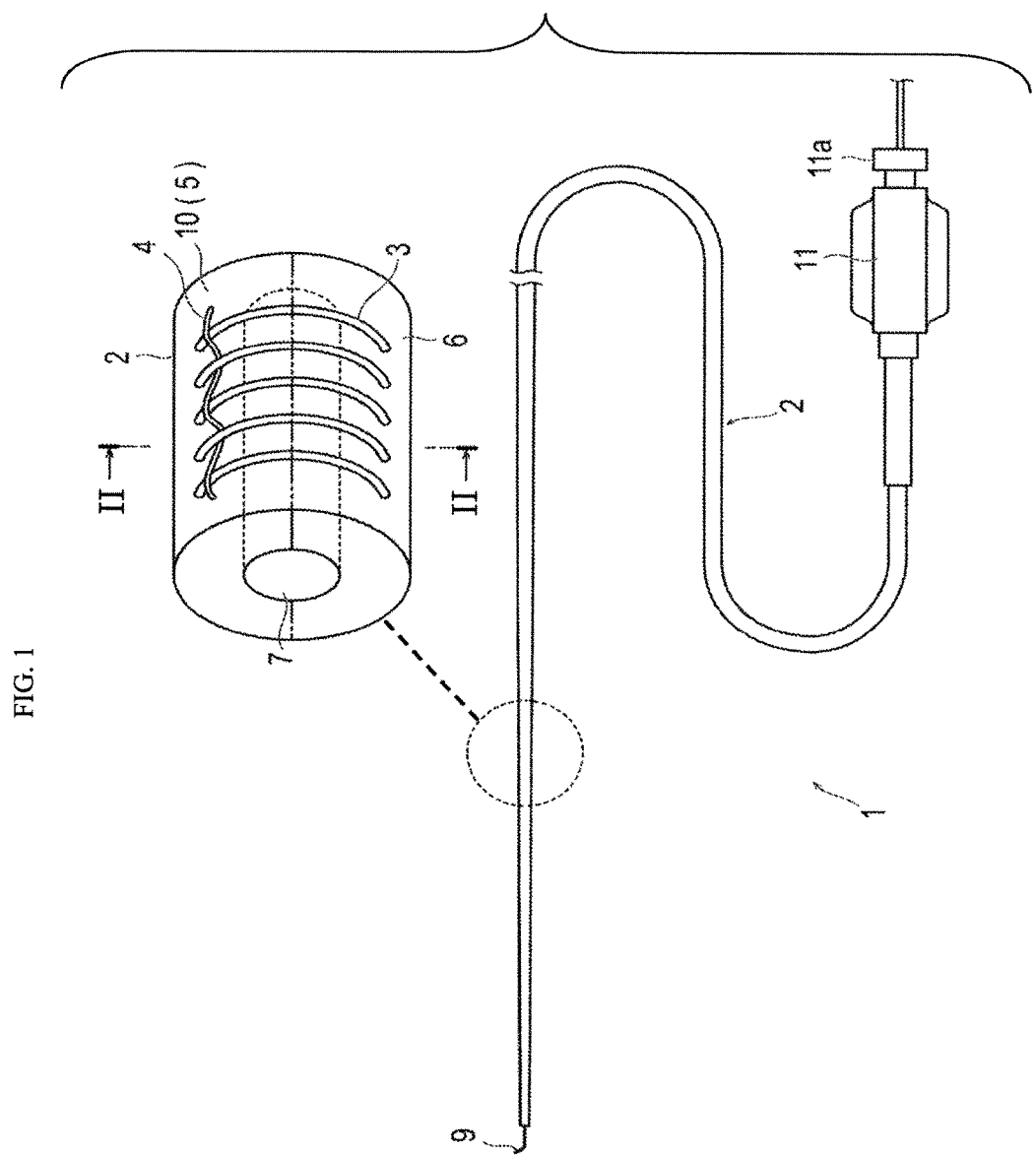
FIG. 1 is a plan view and a partially enlarged view illustrating an overall configuration example of a catheter according to an embodiment (first embodiment) of the present invention.

Hereinafter, embodiments of a catheter and method, representing examples of the inventive catheter and method disclosed here, will be described. The disclosed catheter and method are not limited only to the following embodiments. In some cases, a dimensional ratio in the drawings may be exaggerated and different from a dimensional ratio used in practice in order to facilitate the description.

In addition, in the present description, "X to Y" indicating a range means "X or larger and Y or smaller". The "weight" and the "mass", the "wt %" and the "mass %", and the "part by weight" and the "part by mass" are treated as synonyms. In addition, unless otherwise described, measurement work for operations, physical properties, or the like is carried out under the conditions of room temperature (20° C. to 25° C.) and a relative humidity of 40% to 50%.

[Catheter]

The catheter disclosed here may be used for any desired purpose. In view of a lubricity providing effect and backup capability (improved indwelling or retention ability) when the catheter comes into contact with the body fluid or the blood, the catheter is preferably used while coming into contact with the body fluid or the blood. Specifically, the catheter configuration disclosed here can be applied to various catheters such as a guiding catheter, an angiographic catheter, various balloon catheters for PTCA, PTA, IABP, or the like, an ultrasonic catheter, an atherectomy catheter, an endoscopic catheter, an indwelling catheter, a drug solution administering catheter, and a micro-catheter (catheter for embolization) used in order to administer or inject various therapeutic drugs, embolus materials, contrast agents, or the like into a target area inside a brain, an abdominal organ (for example, a liver), and the like. In particular, it is possible to improve operability and indwelling convenience by using the catheter disclosed here in an easy (i.e., simple) configuration. Accordingly, the catheter configuration disclosed here is suitably applied to a catheter whose diameter needs to be reduced to be used in treating a peripheral blood vessel. Therefore, the catheter is preferably applied to a micro-catheter to be inserted into the peripheral blood vessel which has many bifurcated portions, which meanders in a complicated manner, and whose diameter is narrow, for example, approximately 3 mm or smaller.

The below description relates to a preferred embodiment of a catheter (particularly, a micro-catheter). However, the catheter is not limited to the preferred embodiment and the catheter configuration is applicable to a catheter which is introduced so as to indwell in other body lumens, in the same manner or in a suitably modified manner.

Figure 2:
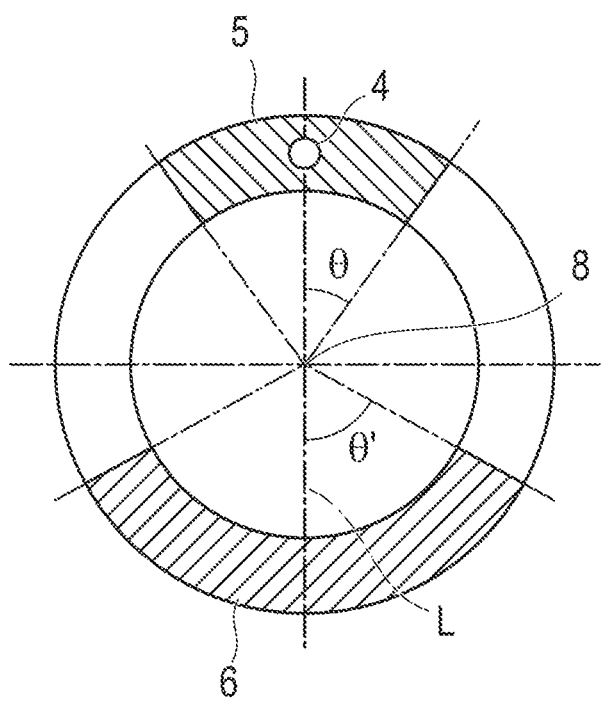
FIG. 2 is a schematic sectional view taken along line II-II of the catheter illustrated in FIG. 1.

FIG. 1 is a plan view and a partially enlarged view illustrating an overall configuration example of a catheter according to an embodiment (first embodiment) of the present invention. FIG. 2 is a schematic sectional view taken along line II-II of the catheter illustrated in FIG. 1. In this description, the end or side at which a user operating the catheter (i.e., the right side in FIG. 1) is referred to as a "proximal end" or a "proximal side", and the end or side inserted into a body lumen of a living body (i.e., the left side in FIG. 1) is referred to as a "distal end" or a "distal side".

A catheter 1 according to the present embodiment includes a flexible and tubular catheter main body 2, a wire member 4 arranged inside (embedded in) the catheter main body 2, a reinforcement member 3 (wire member) arranged inside (embedded in) the catheter main body 2 and a deformable region 10. In addition, a hub 11 serving as an injection port for injecting a therapeutic drug, a contrast agent, or the like is formed in a proximal portion of the catheter main body 2.

The reinforcement member 3 may have any desired shape, but preferably has a coil shape having a reinforcing effect. Here, the coil-shaped reinforcement member is formed by winding or twisting a wire member or rope. Multiple circular rings are formed inside the formed reinforcement member. The reinforcement member 3 may extend in the entire axial direction from a distal end to a proximal end of the catheter main body. In this case, it is preferable that the reinforcement member is embedded in the catheter main body. It is thus possible to manufacture a catheter which has a large inner diameter and a small outer diameter while increasing the strength of the catheter. Here, a winding pitch of the coil may be the same or different from the distal end to the proximal end of the catheter main body. In the latter case, it is preferable that the coil is wound using a relatively large winding pitch in a region on the proximal side, the coil is wound using a relatively small winding pitch in a region on the distal side, and the winding pitch gradually decreases toward the distal side. This structure of gradually decreasing winding pitch decreases rigidity of the catheter in the region on the distal side, compared to the region on the proximal side. For example, the catheter having this form includes a catheter having a coil-shaped reinforcement member which is disclosed in Japanese Patent Application Publication No. JP-A-2001-218851. Although not particularly limited, for example, the method disclosed in the aforementioned Japanese publication can be similarly applied to a manufacturing method of the above-described catheter.

In the present description, the winding pitch of the coil means a distance in a longitudinal direction of the catheter between adjacent winding (roll) and winding (roll) which configure the coil. In other words, the winding pitch is a length of a gap (clearance) between one winding (roll) and the adjacent winding (roll) in the longitudinal direction of the catheter 1.

The deformable region 10 is a region which is relatively less likely to stretch in the circumferential direction of the catheter. Specifically, the deformable region 10 is formed on the same side as the wire member 4. The deformable region 10 is parallel to the lumen of the catheter main body 2 and extends in the axial direction. The coil-shaped reinforcement member and the wire member are disposed in the catheter. The wire member can be positioned to restrict movement of the coil-shaped reinforcement member in a direction where the pitch of the coil is widened. Therefore, when the catheter includes the coil-shaped reinforcement member, the stretching of the catheter on a side having the wire member is restricted. Accordingly, when the catheter is bent, the side having the wire member is located on the inner side (i.e., the inner side of the bent region), and a side opposite to the side having the wire member located on the opposite side with respect to the axis of the lumen of the catheter is located on the outer side (i.e., the outer side of the bent region). That is, when the catheter has the coil-shaped reinforcement member, the side having the wire member is the deformable region located on the inner side when the catheter is bent. In this manner, when the coil-shaped reinforcement body is included in the catheter, it is possible to easily prepare the deformable region by using the wire member (i.e., easily configure one region of the main body to be the deformable region).

Figure 3A:
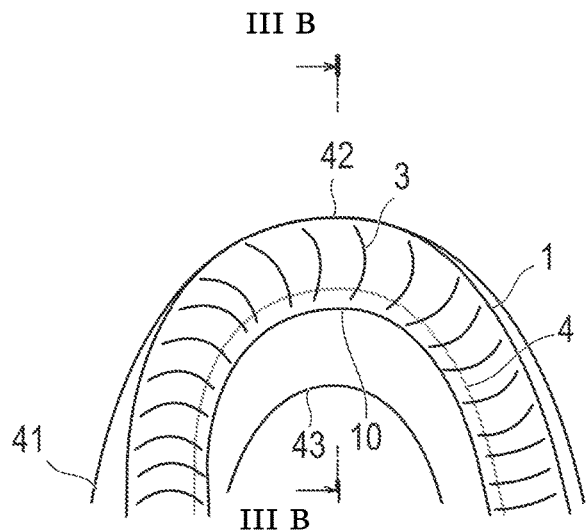
FIGS. 3A-3D are explanatory views schematically illustrating the first embodiment which employs the catheter illustrated in FIG. 1.
Figure 3B:
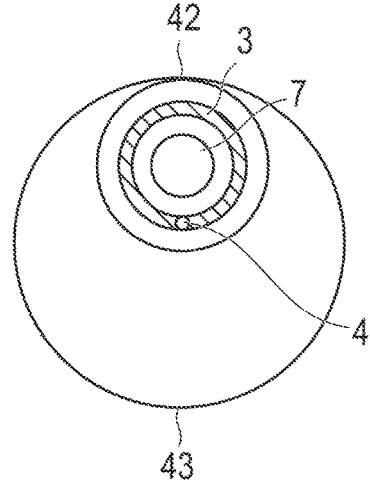
Figure 3C:
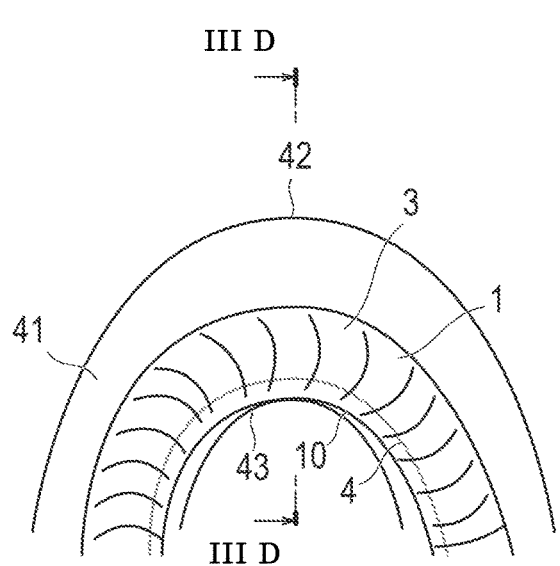
Figure 3D:
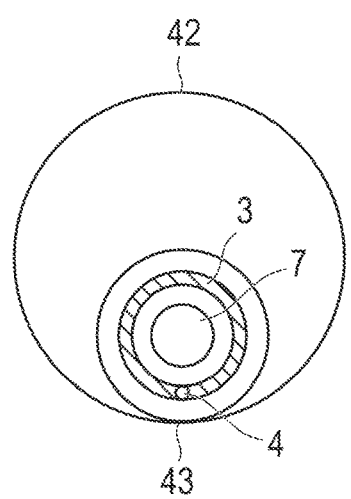

Here, the wire member 4 may have any shape and is configured to include a material having lower rigidity than that of the reinforcement member 3. In FIG. 1, a linear wire member is illustrated as an example of the wire member 4. In a case where the catheter is configured to include the coil-shaped reinforcement member 3 and the wire member 4, the wire member 4 is on the same side (i.e., at the same circumferential region) of the catheter as the deformable region. That is, according to a preferred form, the catheter has the coil-shaped reinforcement member and the wire member extending parallel to the axial direction of the catheter, and the wire member is arranged on the same side as the deformable region. Although details will be further described below, this configuration makes it possible to control a bending direction of the catheter by controlling the elasticity in the axial direction of the catheter. In addition, in a case where the deformable region is configured to include the wire member, it is preferable that the wire member is braided into the reinforcement member. FIG. 1 illustrates the wire member 4 braided into the reinforcement member 3. Accordingly, when the catheter is bent, it is possible to suppress movement of the wire member that changes the position of the deformable region. In addition, it is possible to provide a less invasive and safe catheter by preventing the catheter from having a large diameter. Furthermore, the braided wire restricts stretching of the coil. Accordingly, it is possible to more efficiently restrict coil-shaped reinforcement member movement in the direction where the pitch of the coil is widened. In addition, it is possible to effectively suppress and prevent the wire member from deviating from the reinforcement member (i.e., moving relative to the reinforcement member) due to the deformation caused by the catheter passing through the bent section. Furthermore, it is possible to effectively control the elasticity in the axial direction of the catheter and the bending direction of the catheter. To be more specific, when the reinforcement member has the coil shape, if the deformable region formed by the wire member extends in the axial direction of the catheter, an elastic difference occurs between a side of the catheter surface having the deformable region and a side of the catheter surface having no deformable region (i.e., a surface circumferentially opposite to the surface having the deformable region). To be more specific, the elasticity of the catheter at the deformable region having the wire member is lower than that at the region of the catheter having no wire members. Therefore, as illustrated in FIG. 3A, when the catheter 1 passes through a vascular bent section, the surface opposite to the deformable region having the wire member 4 comes into contact with a vascular inner wall 42 located on the outer side of the vascular bent section. The wire member is extends in the axial direction of the catheter. Accordingly, it is possible to control the bending direction of the catheter by controlling the elasticity in the axial direction of the catheter. Here, it is preferable that the surface lubricating portion (i.e., lubricating layer) is on the surface opposite to the deformable region with respect to the axis of the lumen of the catheter (i.e., the surface which comes into contact with the vascular inner wall 42 on the outer side of the vascular bent section). This decreases friction against the vascular wall. Accordingly, the catheter can be smoothly inserted (operability of the catheter can be improved). In order to more clearly understand the arrangement of the wire member, the catheter is illustrated in FIG. 3B using a schematic sectional view taken along line III B-III B from FIG. 3A. In the schematic sectional view in FIG. 3B, in order to clarify a positional relationship between the reinforcement member 3 and the wire member 4, a catheter substrate (inner layer and outer layer) is illustrated using a white blank, and the reinforcement member 3 is illustrated using a diagonal line. FIGS. 3C and 3D illustrate the catheter fixed at the inner periphery of the vascular bent section in order to inject a therapeutic drug or a contrast agent. To reach this position, the catheter 1 is slightly pulled back (i.e., operated to move proximally), and is unbent (i.e., the radius of curvature after the catheter 1 is moved proximally is less than the radius of curvature when the catheter is being moved distally and contacting the inner wall 42 on the outer side of the vascular bent section) to fix the catheter 1 to a vascular inner wall 43 on the inner side of the vascular bent section. Here, it is preferable that the less lubricious portion is disposed on the same side of the catheter as the deformable region with respect to the axis of the lumen of the catheter which comes into contact with the vascular inner wall 43 on the inner side of the vascular bent section. This configuration increases friction against the vascular wall. Accordingly, the catheter can be firmly fixed at a predetermined position (i.e., so that the catheter can be retained in place and indwelling convenience/backup capability can be improved). In order to more clearly understand the arrangement of the wire member, the catheter is illustrated in FIG. 3D using a schematic sectional view taken along line III D-III D from FIG. 3C. In the schematic sectional view, in order to clarify a positional relationship between the reinforcement member 3 and the wire member 4, a catheter substrate (inner layer and outer layer) is illustrated using a white blank, and the reinforcement member is illustrated using a diagonal line. Therefore, according to the above-described configuration, it is possible to more effectively improve operability when the catheter is introduced into a desired position and indwelling convenience (retention/backup capability) at the desired position. That is, it is preferable that the reinforcement member is coil shaped and the less lubricious portion is arranged on the same circumferential side of the catheter as the deformable region with respect to the axis of the lumen.

In FIG. 1, one wire member 4 is present so as to be parallel to the lumen of the catheter main body 2 and to extend in the axial direction. However, the present invention is not limited to one wire member. Multiple wire members may extend parallel to the lumen of the catheter main body 2 and in the axial direction. In this case, the multiple wire members may be arranged so as to be eccentric to the central axis (axis) of the catheter main body (that is, biased to one side). The region having the biased wire members arranged in this embodiment is the deformable region. The number of arranged wire members is not particularly limited, but in view of easy production/manufacturability, a reduced diameter, or the like, the number of wire members is preferably 1 to 8, and more preferably 1 to 4.

At least a portion of the outer surface of the catheter main body 2 is covered with a surface lubricating portion 6 and a less lubricious portion 5 (i.e., the less lubricious portion 5 is relatively less lubricious than the surface lubricating portion 6). Here, the surface lubricating portion 6 and the less lubricious portion 5 are located at the same position in the axial direction of the catheter (i.e., the surface lubricating portion 6 is at the same axial position but is at a different circumferential position on the outer surface than the less lubricious portion 5). Here, since the surface lubricating portion is present, the catheter is provided with lubricity in an aqueous liquid such as body fluid or blood. The catheter can be easily inserted into the body lumen, for example. Accordingly, operability can be improved. In addition, since the catheter is covered with the surface lubricating portion, it is possible to minimize damage to tissue mucous membranes during an operation of introducing the catheter into the body lumen. For a less invasive catheter, the friction coefficient of the surface lubricating portion is preferably in a range from 0.01 and smaller than 0.3, and more preferably 0.03 to 0.2. Here, the disclosed catheter includes both the surface of a substrate (catheter main body) configuring the catheter having partial or entire surface lubricity. All of the surface (entire surface) of the catheter does not need to have lubricity. However, it is preferable that the surface lubricating portion is formed on at least a surface portion (partially in some cases, or entirely in other cases) which comes into contact with the body fluid or the blood. Therefore, for example, the proximal portion side of the catheter may not have the surface lubricating layer. In addition to the outer surface of the catheter main body, the lumen (inner wall of the lumen) of the catheter may have the surface lubricating layer. In a case where the catheter has multiple lumens, the surface lubricating portion may be disposed in all of the lumens, or the surface lubricating portion may be disposed in some of the lumens. In addition, the surface lubricating portion does not need to be disposed on the entire surface of the lumen (inner wall of the lumen) of the catheter. The surface lubricating portion may instead be only partially disposed on the inner wall of the lumen.

The less lubricious portion has low surface lubricity (i.e., is relatively less lubricious compared to the surface lubricating portion), and is installed on the outer surface of the catheter at the same position in the axial direction as the surface lubricating portion 6. Here, in view of backup capability (i.e., to promote indwelling or retention of the catheter) of the less lubricious portion, the friction coefficient of the less lubricious portion is preferably 0.3 to 4, and more preferably 0.5 to 3. In this manner, while operability is satisfactorily ensured, the backup capability is achieved when the catheter is indwelled at a predetermined position inside the body lumen (for example, the blood vessel). Accordingly, the catheter can be firmly held at the predetermined position. In the present description, the "friction coefficient" means a value measured by the following method.

(Method of Measuring Friction Coefficient)

Figure 10:
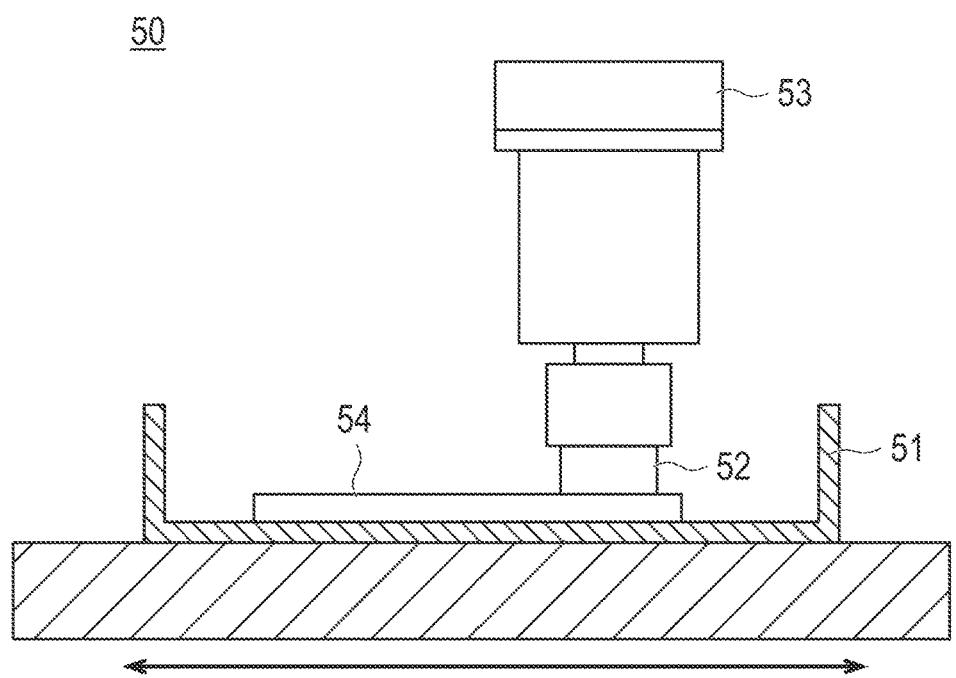
FIG. 10 is a schematic view of a surface lubricity evaluation test device (friction measuring instrument).

A core bar is inserted into the catheter which is cut to have a sufficient length for measurement, and is formed into a linear shape. Such a catheter is used as a sample 54. As illustrated in FIG. 10, double-sided tape adheres to a rear surface of a glass laboratory dish 51, and the sample 54 is fixed to the glass laboratory dish 51 so that a measurement surface of the sample is located above. The glass laboratory dish 51 is filled with pure water, and is set on a sample stage of a friction measuring instrument 50 (e.g., made by Trinity Laboratories Ltd., Handy Tribo Master TL201). A load of 200 g is applied to a cylindrical rubber terminal ($\phi$=10 mm) 52 by a weight 53. A sliding resistance value (first sliding resistance value) (gf) is measured after the sample reciprocates once at a speed of 1,000 mm per minute for moving the sample a distance of 10 mm. The evaluations are performed with n=3, and an average of the evaluations is set to be the sliding resistance value. The sliding resistance value is divided by a value of the load to obtain the friction coefficient. When the length of the region to be measured is shorter than 10 mm, the movement distance may be appropriately changed to match the measurement length.

The installation length of the surface lubricating portion and the less lubricious portion is not particularly limited as long as desired operability and backup capability can be achieved. The installation length of the surface lubricating portion and the less lubricious portion is preferably 100 mm to 1,000 mm, and more preferably 300 mm to 900 mm. According to this installation length, while operability is satisfactorily ensured when the catheter is inserted, improved backup capability can be achieved since the less lubricious portion efficiently and more reliably comes into contact with the body lumen wall when the catheter indwells in the body lumen.

The surface lubricating portion and the less lubricious portion are formed on the outer surface of the catheter at the same position in the axial direction of the catheter. Here, the "same position in the axial direction of the catheter" means that both the surface lubricating portion and the less lubricious portion are formed on a cross section at a certain position of the catheter. The position for forming the surface lubricating portion and the less lubricious portion on the outer surface of the catheter is not particularly limited as long as both of these are located at the same position in the axial direction of the catheter. The surface lubricating portion and the less lubricious portion positions vary depending on the shape of the catheter, an introducing position, an indwelling position, or the like. In FIG. 1, the less lubricious portion 5 is formed on a half of the outer surface of the catheter around the deformable region, and the surface lubricating portion 6 is formed on the remaining half of the outer surface of the catheter. However, the disclosed catheter is not limited to this form. Specifically, in a case where one wire member 4 is parallel to the lumen of the catheter main body 2 and extends in the axial direction, the less lubricious portion 5 is formed so that an angle ("θ" in FIG. 2) formed between a line connecting the center of the wire member 4 and an axis 8 of the catheter and a line connecting an end portion in the circumferential direction of the less lubricious portion 5 and the axis 8 of the catheter is preferably ±5° to ±90°, and more preferably ±15° to ±90°. In addition, in a case where multiple wire members 4 are parallel to the lumen of the catheter main body 2 and extend in the axial direction so as to be eccentric to the central axis (axis), the less lubricious portion 5 is formed so that an angle formed between a line connecting a center point of two wire members farthest away from each other and the axis 8 of the catheter and a line connecting an end portion in the circumferential direction of the less lubricious portion 5 and the axis 8 of the catheter is preferably ±5° to ±90°, and more preferably ±15° to ±90°. If the less lubricious portion is formed in this state, backup capability (indwelling convenience) can be further improved. In addition, the surface lubricating portion 6 is formed so that an angle ("θ'" in FIG. 2) between the extension line of the line (line "L" in FIG. 2) connecting the center of the wire member 4 and the axis 8 of the catheter and a line connecting an end portion in the circumferential direction of the surface lubricating portion 8 is preferably ±5° to ±90°, and more preferably ±15° to ±90°. When multiple wire members 4 are present, the above-described angle is also set to be an angle formed between the extension line of the line connecting the center point of two wire members farthest away from each other and the axis 8 of the catheter and the line connecting the end portion in the circumferential direction of the surface lubricating portion 8 and the axis 8 of the catheter. Operability can be further improved by forming the lubricating portion as described above. Therefore, since the less lubricious portion and the surface lubricating portion are present in this area (i.e., along a common axial extent), the catheter can also be smoothly inserted into the bent section, and the catheter can be more firmly held at a predetermined position inside the body lumen (for example, the blood vessel). In addition, the above-described angles θ and θ' may be the same size, or may be respectively different sizes.

The catheter main body 2 is configured to include a flexible and tubular member, and internally has a lumen 7 extending from the proximal end to the distal end in the axial direction. The lumen 7 functions as a lumen for a guide wire. As illustrated in FIG. 1, a guide wire 9 is inserted into the lumen 7 when the catheter 1 is inserted into the blood vessel. In addition, the lumen 7 can be used to allow passage of a drug solution, an embolus material, a contrast agent, or the like.

The hub 11 functions as an insertion port for inserting the guide wire 9 into the lumen 7, and an injection port or the like for injecting the drug solution, the embolus material, the contrast agent, or the like into the lumen 7. The hub 11 also functions as a gripping portion (for a user) when the catheter 1 is operated.

In addition, a catheter distal portion is a portion extending from the catheter main body, and can employ various known structures in the related art. For example, the distal portion may have a shape bent in a loop shape, or may have a substantially linear shape. In addition, a member for providing functions such as cleaning, aspirating, lighting, and imaging, may be attached to the distal portion.

Although not particularly limited, the catheter main body 2 is normally a flexible material. Examples include polyolefin such as polypropylene, and ethylene-vinyl acetate copolymer, polyester such as polyamide, polyethylene terephthalate (PET), and polybutylene terephthalate (PBT), fluorine-based resins such as polyurethane, polyvinyl chloride, polystyrene-based resins, polytetrafluoroethylene, and ethylene-tetrafluoroethylene copolymer, various flexible resins such as polyamide elastomer, polyurethane elastomer, polystyrene elastomer, polyester elastomer, and fluorine-based elastomer, rubber materials such as silicone rubber, and latex rubber, or a combination of two or more materials.

The catheter main body 2 may have a proximal side portion and a distal side portion located on the distal side further from (i.e., distal to) the proximal side portion. In this embodiment, it is preferable that the distal side portion has lower rigidity than the proximal side portion. For example, the proximal side portion of the catheter main body 2 may be a relatively high rigid material within the above-described configuration materials, and the distal side portion of the catheter main body 2 may be a relatively low rigid material within the above-described configuration materials (i.e., the material of the distal side portion is relatively less rigid than the proximal side portion material). This improves the following ability of the catheter.

The structure of the catheter main body is not particularly limited, but the catheter main body may have a structure that includes an inner layer and an outer layer, and in which the wire member (wire members) forming the reinforcement member and the deformable region are embedded between the inner layer and the outer layer. In this case, the inner layer covers an inner periphery of the reinforcement member (coil), serves as a core for arranging the reinforcement member, and forms the lumen. As the inner layer, it is possible to use the same configuration material as the outer layer (details to be described below). However, it is preferable that the inner layer is configured to include a low friction material. Friction can thus be reduced on the inner surface of the inner layer, to reduce sliding resistance against the guide wire inserted into the lumen. Accordingly, it is possible to more easily and smoothly perform an operation for inserting the catheter into the blood vessel along the preceding guide wire or an operation for removing the guide wire from the catheter.

Specifically, the low friction material for configuring the inner layer is not particularly limited as long as the material can reduce friction on the inner surface of the inner layer. For example, the material includes a fluorine-based resin, Nylon 66, polyether ether ketone, high density polyethylene, or the like. Among these materials, it is more preferable to use the fluorine-based resin. For example, the fluorine-based resin includes polytetrafluoroethylene, polyvinylidene fluoride, ethylene-tetrafluoroethylene, perfluoroalkoxy resins, and the like. Polytetrafluoroethylene is preferable among these materials. Although not particularly limited, for example, for a reduced diameter, the thickness of the inner layer 7 is preferably 5 μm to 50 μm, and more preferably 5 μm to 40 μm.

Although not particularly limited, the material of the outer layer is normally a flexible material. For example, it is possible to use polyolefin such as polypropylene, and ethylene-vinyl acetate copolymer, polyester such as polyamide, polyethylene terephthalate (PET), and polybutylene terephthalate (PBT), fluorine-based resins such as polyurethane, polyvinyl chloride, polystyrene-based resins, polytetrafluoroethylene, and ethylene-tetrafluoroethylene copolymer, various flexible resins such as polyamide elastomer, polyurethane elastomer, polystyrene elastomer, polyester elastomer, and fluorine-based elastomer, rubber materials such as silicone rubber, and latex rubber, or a combination of two or more materials. Although not particularly limited, for example, for a reduced diameter, the thickness of the outer layer is preferably 0.05 mm to 0.15 mm, and more preferably approximately 0.06 mm to 0.12 mm. The catheter can achieve sufficient pushing performance and torque transmission performance when the outer layer is within the described thicknesses.

Although not particularly limited, the reinforcement member includes a material configured to include at least either a metal member or a non-metal member. For example, it is possible to use a material having the metal member formed in a helical shape, a material having the non-metal member formed in a helical shape, and a material having the metal member and the non-metal member which are superimposed on each other and formed in a helical shape or the like. For example, the metal member material can be one of, or a combination of two or more of, stainless steel, a nickel-titanium alloy, platinum, iridium, tungsten, and the like. The non-metal member material can be one of, or a combination of two or more of, carbon, polyamide, polyethylene terephthalate, polybutylene terephthalate, and the like. It is preferable to configure the reinforcement member to include a radiopaque material such as tungsten, platinum, iridium, and an alloy containing these materials. Including a radiopaque material allows the catheter to be satisfactorily visible under X-ray fluoroscopy. The reinforcement member may be configured to include the same material or may be configured to include a different material.

A cross-sectional shape of the reinforcement member is not particularly limited, and may have any desired shape such as a circular shape, and a flat shape (ribbon shape, belt shape).

The thickness of the reinforcement member is not particularly limited. For example, when the reinforcement member has a circular cross-sectional shape, the diameter is preferably approximately 10 μm to 100 μm, and more preferably approximately 30 μm to 60 μm. In addition, when the reinforcement member has a ribbon shaped cross-section, the reinforcement member preferably has the width of approximately 0.1 mm to 1.0 mm, and the thickness of approximately 0.04 mm to 0.05 mm. Since the reinforcement member is arranged in this way, a sufficient reinforcing effect can be obtained through a relatively thin thickness. Accordingly, the diameter of the catheter is advantageously reduced.

Although not particularly limited, for example, a winding pitch of the reinforcement member is preferably 50 μm to 500 μm, and more preferably 80 μm to 350 μm. If the winding pitch falls within this range, the catheter shows sufficient flexibility (low rigidity), and can be sufficiently bent along the bending sections of the blood vessel (body cavity). Accordingly, it is possible to improve followability (i.e., maneuverability) of the catheter.

Although not particularly limited, the wire member for forming the deformable region can include at least either a metal member or a non-metal member. For example, it is possible to use a material having the metal member formed in a helical shape, a material having the non-metal member formed in a helical shape, and a material having the metal member and the non-metal member which are superimposed on each other and formed in a helical shape or the like. For example, as the metal member material can be one of, or a combination of two or more of, stainless steel, a nickel-titanium alloy, platinum, iridium, tungsten, and the like. The non-metal member material can be one of, or a combination of two or more of, carbon, polyamide, polyethylene terephthalate, polybutylene terephthalate, and the like. It is preferable to configure the wire member to include a radiopaque material such as tungsten, platinum, iridium, and an alloy containing these materials. In this manner, the catheter is satisfactorily visible under X-ray fluoroscopy. In addition, elasticity in the axial direction of the catheter can be more easily controlled. The wire member may be configured to include the same material as that of the reinforcement member, or may be configured to include a material different from that of the reinforcement member.

A cross-sectional shape of the wire member for forming the deformable region is not particularly limited, and may have any desired shape such as a circular shape, and a flat shape (ribbon shape, belt shape). The cross-sectional shape of the wire member may be the same as that of the reinforcement member, or may be different therefrom.

The thickness of the wire member for forming the deformable region is not particularly limited. For example, when the wire member has a circular cross-sectional shape, the diameter is preferably approximately 10 μm to 100 μm, and more preferably approximately 30 μm to 60 μm. When the wire member has a ribbon cross-sectional shape, the wire member preferably has the width of approximately 0.1 mm to 1.0 mm, and the thickness of approximately 0.04 mm to 0.05 mm. Elasticity of the catheter can be easily controlled by arranging the wire member in this way. In addition, the diameter of the catheter is advantageously reduced. The thickness of the wire member may be the same as that of the reinforcement member, or may be different.

The reinforcement member has been described in detail above as possessing a coil shape. However, the catheter disclosed here is not limited to having a coil-shaped reinforcement member. For example, the reinforcement member may have a mesh shape. That is, according to another embodiment, the catheter has the mesh-shaped reinforcement member and the wire member extends parallel to the axial direction of the catheter. The wire member is arranged on a side opposite to the deformable region with respect to the axis of the lumen of the catheter (i.e., circumferentially opposite with respect to the axis of the lumen). Here, the mesh-shaped reinforcement member is formed by braiding multiple reinforcement members having a shape of wire members or ropes. Specifically, the mesh shape is created by braiding the multiple reinforcement members in a grid pattern. The adjacent reinforcement members may have a gap formed therebetween, or may not have the gap. Since the mesh-shaped reinforcement member and the wire member are disposed in the catheter, it is possible to increase rigidity on the side having the wire member. That is, when the reinforcement member is mesh shaped, unlike a case where the reinforcement member is coil shaped, reinforcement members (for example, a first reinforcement member and a second reinforcement member in FIG. 4) forming the mesh-shaped reinforcement member partially overlap each other in a braided state, thereby restricting the movement of the reinforcement member. Therefore, the presence or absence of the wire member does not significantly affect elasticity of the reinforcement member, but causes the catheter to have hardened physical properties (i.e., is relatively more rigid) on the circumferential side having the wire member. Therefore, when the catheter has the mesh-shaped reinforcement member, a portion on the side having the wire member is hardened, and the catheter is less likely to be bent. Accordingly, the side having the wire member is located on the outer side, and the side opposite to the side having the wire member located on the opposite side with respect to the axis of the lumen of the catheter is located on the inner side. In other words, when the catheter has the mesh-shaped reinforcement member, the side opposite to the wire member with respect to the axis of the lumen of the catheter is the deformable region located on the inner side when the catheter is bent. As described above, even when the mesh-shaped reinforcement body is used, it is possible to easily prepare the deformable region by using the wire member (i.e., the location of the deformable region can be easily controlled by the circumferential position of the wire member in the main body of the catheter).

The catheter having the reinforcement member in a mesh shape is described below.

Figure 9:
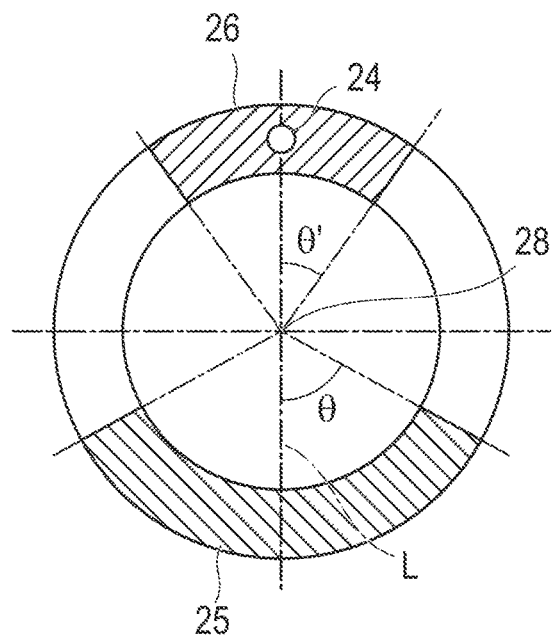
FIG. 9 is a schematic sectional view taken along line IX-IX of the catheter illustrated in FIG. 4.

FIG. 4 is a plan view and a partially enlarged view illustrating an overall configuration example of a catheter according to another embodiment (second embodiment) of the present invention. FIG. 9 is a schematic sectional view taken along line IX-IX of the catheter illustrated in FIG. 4. Hereinafter, the right side of FIG. 4 is referred to as a "proximal end", and the left side of FIG. 4 is referred to as a "distal end".

A catheter 21 according to the present embodiment includes a flexible and tubular catheter main body 22, and a reinforcement member 23 and a wire member 24 which are arranged inside the catheter main body 22. In the catheter according to the present embodiment, the wire member 24 is not present in a deformable region 30. It is preferable that the deformable region 30 is on a side opposite to the wire member 24 with respect to the axis of the lumen of the catheter. In addition, the hub 11 serving as an injection port for injecting a therapeutic drug, a contrast agent, or the like is formed in a proximal portion of the catheter main body 22. A lumen extending from the proximal end to the distal end is in the catheter main body 22. When the catheter 21 is inserted into the blood vessel, a guide wire is inserted into the lumen. In addition, the lumen is also used as a flow path of the contrast agent, a drug solution, or the like.

Figure 6:
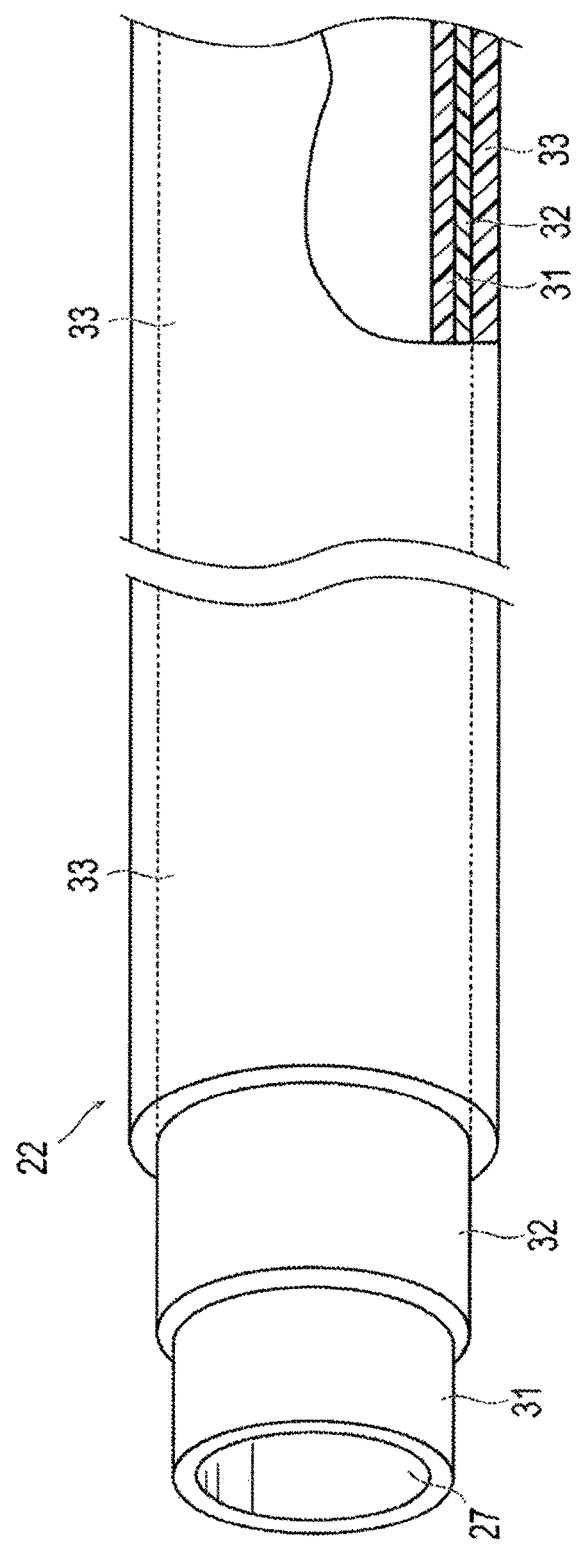
FIG. 6 is an explanatory view schematically illustrating another structural example of the catheter illustrated in FIG. 4.

As illustrated in FIG. 5, the catheter main body 22 has an intermediate layer 32 around a substrate tube (inner layer) 31 which is a tubular member. As illustrated in FIG. 6, when necessary, an outer layer 33 may be further formed around the intermediate layer 32. In FIGS. 5 and 6, the reinforcement member and the wire member (not illustrated) are formed in the intermediate layer 32. In addition, a distal portion 27 of the catheter main body 22 may not have the intermediate layer 32, and may be configured to include only the substrate tube (inner layer) 31. In this case, the distal portion 27 may be configured to include the substrate tube (inner layer) 31 and the outer layer 33.

As illustrated in FIG. 4, the hub 11 is mounted on the proximal end of the catheter main body 22. The hub 11 functions as an insertion port for inserting the guide wire into the lumen, and an injection port for injecting the drug solution or the like into the lumen. The hub 11 also functions as a gripping portion when the catheter is operated.

Figure 7A:
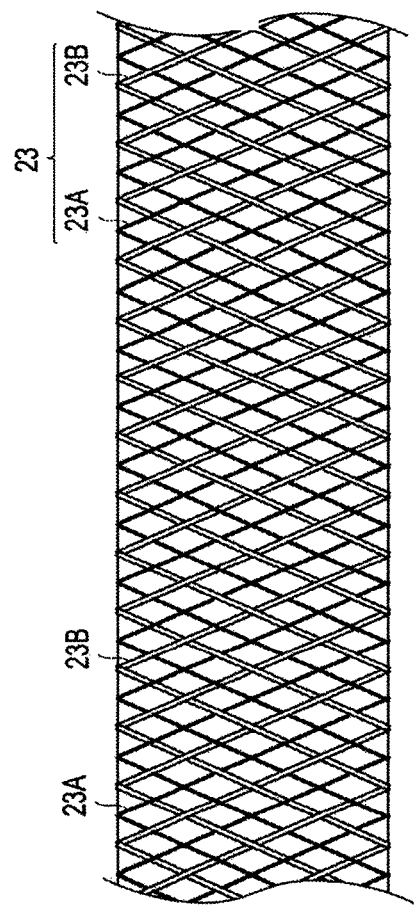
FIGS. 7A and 7B are partially enlarged views of another example of the reinforcement member of the catheter illustrated in FIG. 4.
Figure 7B:
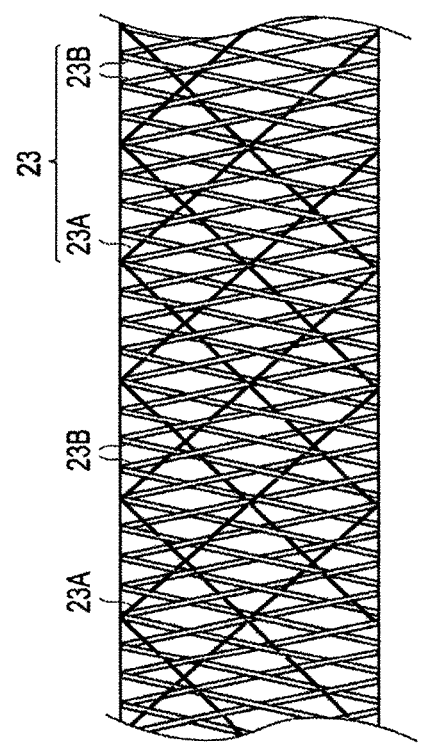

The intermediate layer 32 is configured to include the reinforcement member 23 and the wire member 24. In this case, the reinforcement member 23 may have any desired shape, but preferably has a mesh shape to provide a reinforcing effect. The reinforcement member 23 may extend in the axial direction along the entire axial extent of the catheter main body from the distal end to the proximal end of the catheter main body. The mesh-shaped reinforcement member 23 is configured to include a first reinforcement member 23A and a second reinforcement member 23B. Here, the first reinforcement member 23A and the second reinforcement member 23B may be formed of any desired material (for example, a resin material and a metal material). In addition, the above-described materials may be the same as each other, or may be different from each other. In addition, braiding density of the first reinforcement member 23A and the second reinforcement member 23B is not particularly limited. For example, braiding density possibilities include the first reinforcement member 23A and the second reinforcement member 23B being braided with substantially the same density as illustrated in FIG. 4, the first reinforcement member 23A being densely braided and the second reinforcement member 23B being sparsely braided as illustrated in FIG. 7A, the first reinforcement member 23A being sparsely braided and the second reinforcement member 23B being densely braided as illustrated in FIG. 7B. In FIGS. 7A and 7B, a less lubricious portion 25, a surface lubricating portion 26, and the wire member 24 are omitted. For example, the catheter having these forms includes the catheter having the reinforcement member of the mesh shape (braided shape) disclosed in Japanese Patent Application Publication No. JP-A-2001-87389. Although not particularly limited, for example, the method disclosed in Japanese Patent Application Publication No. JP-A-2001-87389 (e.g., paragraphs [0119] to [0101]) can be similarly applied to a manufacturing method of the above-described catheter.

Figure 8A:
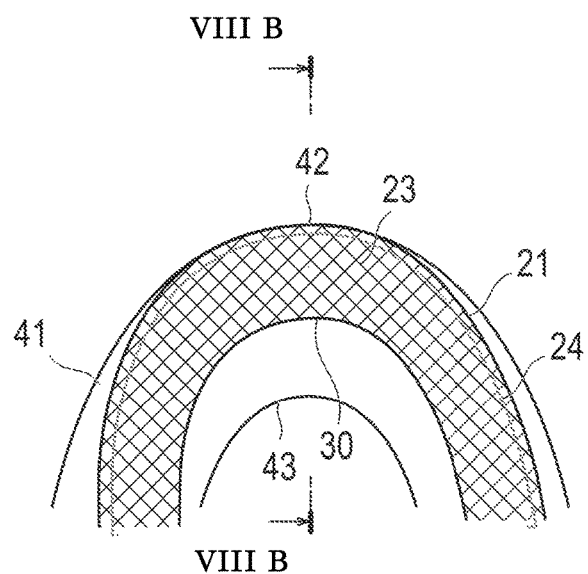
FIGS. 8A-8D are explanatory views schematically illustrating the first embodiment which employs the catheter illustrated in FIG. 4.
Figure 8B:
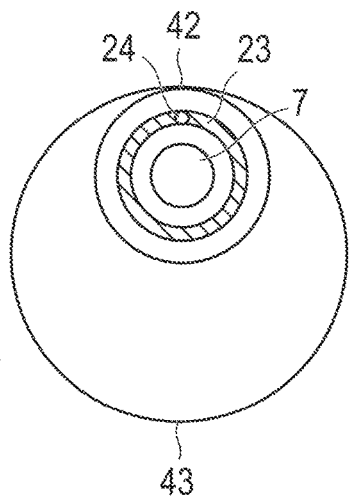
Figure 8C:
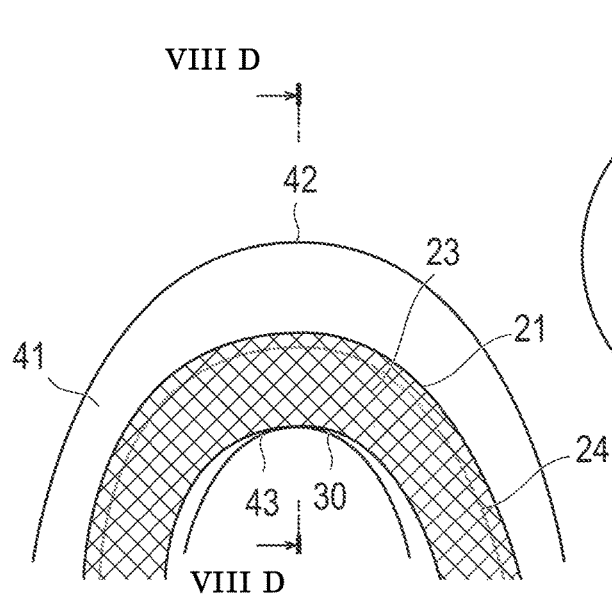
Figure 8D:
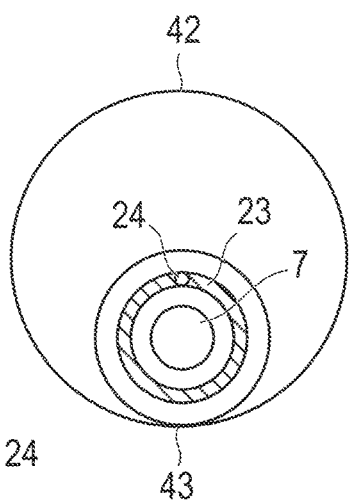

The deformable region 30 is a region which is relatively likely to contract in the circumferential direction of the catheter (i.e., the deformable region 30 is more likely to contract than the region on the side circumferentially opposite to the deformable region 30). Specifically, the deformable region 30 is formed on the opposite side with respect to the axis of the lumen of the catheter, to the wire member which extends parallel to the lumen (particularly, the intermediate layer 32) of the catheter main body 22 in the axial direction. Here, the wire member may have any desired shape, but it is preferable to configure the wire member to have a rigidity lower than that of the reinforcement member. In addition, in a case where the reinforcement member has the mesh shape, the deformable region is configured to be located on a side opposite to the wire member with respect to the axis of the lumen of the catheter. That is, according to a preferred form, the catheter has the mesh-shaped reinforcement member and the wire member extending parallel to the axial direction of the catheter, and the wire member is arranged on the side opposite to the deformable region with respect to the axis of the lumen of the catheter. Although details will be described below, the present embodiment makes it is possible to control a bending direction of the catheter by controlling rigidity in the axial direction of the catheter. In addition, it is preferable that the wire member is braided into the reinforcement member. Accordingly, when the catheter is bent, it is possible to suppress wire member movement that changes the position of the deformable region. In addition, it is possible to provide a less invasive and safe catheter by preventing the catheter from having a large diameter. It is also possible to effectively suppress and prevent the wire member from deviating from the reinforcement member (i.e., moving relative to the reinforcement member) due to the deformation caused by the catheter passing through the bent section. Furthermore, it is possible to effectively control the elasticity in the axial direction of the catheter and the bending direction of the catheter. To be more specific, when the reinforcement member is mesh shaped and the wire member extends in the axial direction, a rigidity difference occurs between a catheter side surface having the wire member (particularly, a surface opposite to the side surface having the deformable region) and a catheter side surface having no wire members (particularly, a surface opposite to the side surface having the deformable region formed by the wire member). Two reinforcement members (first reinforcement member and second reinforcement member) are braided to create the mesh-shaped reinforcement member. Accordingly, when the catheter is deformed, the reinforcement member is less likely to move compared to the coil-shaped reinforcement member. Therefore, when the reinforcement member has the mesh shape, the bending direction of the catheter is determined by the rigidity of the catheter. Therefore, as illustrated in FIG. 8A, when the catheter 21 passes through the vascular bent section, the outer surface on the portion of the main body having the wire member 24 comes into contact with the vascular inner wall 42 on the outer side of the vascular bent section. The wire member is disposed in the axial direction of the catheter in this manner (i.e., extending in the axial direction, but offset from the longitudinal axis of the lumen in the circumferential direction). Accordingly, it is possible to control the bending direction of the catheter by controlling the rigidity in the axial direction of the catheter. Here, it is preferable that the surface lubricating portion is disposed on the side opposite to the deformable region with respect to the axis of the lumen of the catheter. The surface lubricating portion is on the outer surface at the region of the main body of the catheter which comes into contact with the vascular inner wall 42 on the outer side of the vascular bent section. The surface lubricating portion decreases friction (i.e., the friction force applied) against the vascular wall. Accordingly, the catheter can be smoothly inserted (operability of the catheter can be improved). In order to more clearly understand the arrangement of the wire member, the catheter is illustrated in FIG. 8B using a schematic sectional view taken along line VIII B-VIII B from FIG. 8A. In the schematic sectional view FIG. 8B, in order to clarify a positional relationship between the reinforcement member 3 and the wire member 4, a catheter substrate (inner layer and outer layer) is illustrated using a white blank, and the reinforcement member is illustrated using a diagonal line. In addition, the reinforcement member 3 has the mesh shape. Thus, a cross section of the catheter does not have a circular shape as illustrated by FIG. 8B. However, in order to clearly illustrate a position of the reinforcement member 3, the cross section is illustrated in a circular shape. On the other hand, in a case where the catheter is fixed at the inner periphery of the vascular bent section in order to inject a therapeutic drug or a contrast agent, as illustrated in FIG. 8C, the catheter 21 is slightly pulled back (i.e., moved proximally), and is unbent to fix (i.e., retain) the catheter 21 to the vascular inner wall 43 on the inner side of the vascular bent section. Here, it is preferable that the less lubricious portion is disposed on the same side as the deformable region with respect to the axis of the lumen of the catheter which comes into contact with the vascular inner wall 43 on the inner side of the vascular bent section. This increases friction against the vascular wall. Accordingly, the catheter can be firmly fixed at a predetermined position (indwelling convenience/backup capability can be improved). In order to more clearly understand the arrangement of the wire member, the catheter is illustrated in FIG. 8D using a schematic sectional view taken along line VIII D-VIII D from FIG. 8C. In the schematic sectional view in FIG. 8D, in order to clarify a positional relationship between the reinforcement member 3 and the wire member 4, a catheter substrate (inner layer and outer layer) is illustrated using a white blank, and the reinforcement member is illustrated using a diagonal line. In addition, in the form, similarly to FIG. 8B, in order to clearly illustrate a position of the reinforcement member 3, the cross section in FIG. 8D is illustrated in a circular shape. Therefore, according to the above-described configuration, it is possible to more effectively improve operability when the catheter is introduced into a desired position and improve indwelling convenience (i.e., improve retention/backup capability) at the desired position. When the reinforcement member has the mesh shape, it is preferable that the wire member is arranged on a side opposite to the deformable region with respect to the axis of the lumen of the catheter and the less lubricious portion is arranged in the deformable region.

In FIG. 4, one wire member 24 is extends parallel to the lumen of the catheter main body 22 in the axial direction. However, the present invention is not limited to one wire member. Multiple wire members may be used to extend parallel to the lumen of the catheter main body 22 in the axial direction. In this case, the multiple wire members may be arranged so as to be eccentric to the central axis (axis) of the catheter main body (that is, biased to one side). In this case, a region having the biased wire members arranged therein is the deformable region. In addition, the number of arranged wire members is not particularly limited. However, in view of easy production/manufacturability, a reduced diameter, or the like, the number of wire members is preferably 1 to 8, and more preferably 1 to 4.

At least a portion of the outer surface of the catheter main body 22 is covered with the surface lubricating portion 26 and the less lubricious portion 25. Here, the surface lubricating portion 26 and the less lubricious portion 25 are located at the same position in the axial direction of the catheter. The catheter is provided with lubricity in an aqueous liquid such as body fluid and blood because the surface lubricating portion is present. The catheter can be easily inserted into the body lumen, for example. Accordingly, operability can be improved. In addition, since the catheter is covered with the surface lubricating portion, it is possible to minimize damage to tissue mucous membranes during an operation for introducing the catheter. From a viewpoint of the less invasive catheter, the friction coefficient of the surface lubricating portion is preferably in a range from 0.01 and smaller than 0.3, and more preferably 0.03 to 0.2. Here, the disclosed catheter includes the surface of a substrate (catheter main body) having partial or entire surface lubricity. All of the surface (entire surface) of the catheter does not need to have lubricity. However, it is preferable that the surface lubricating portion is formed on at least a surface portion (partially in some cases, or entirely in other cases) which contacts the body fluid or the blood. Therefore, for example, the surface lubricating portion (and the less lubricious portion 25) may not be formed on the proximal portion side of the catheter. In addition to the outer surface of the catheter main body, the surface lubricating portion may be formed in the lumen (i.e., on the inner wall of the lumen) of the catheter. In a case where the catheter has multiple lumens, the surface lubricating portion may be disposed in all of the lumens, or the surface lubricating portion may be disposed in some of the lumens. In addition, the surface lubricating portion does not need to be disposed on the entire surface of the lumen (inner wall of the lumen) of the catheter, but can be only partially disposed on the inner wall of the lumen. In a case where the surface lubricating portion is disposed in the lumen (inner wall of the lumen) of the catheter, it is not necessary to dispose the less lubricious portion at the same position in the axial direction of the catheter.

The less lubricious portion has low surface lubricity (i.e., the less lubricious portion is relatively less lubricious than the surface lubricating portion), and is installed on the outer surface of the catheter at the same position in the axial direction as the surface lubricating portion 26. Here, in view of backup capability (indwelling convenience) of the less lubricious portion, the friction coefficient of the less lubricious portion is preferably 0.3 to 4, and more preferably 0.5 to 3. In this manner, while operability is satisfactorily ensured, the backup capability (i.e., ability to retain the catheter in place) is excellently achieved when the catheter is caused to indwell at a predetermined position inside the body lumen (for example, the blood vessel). Accordingly, the catheter can be firmly held at the predetermined position.

The installation length of the surface lubricating portion and the less lubricious portion is not particularly limited as long as desired operability and backup capability can be achieved. The installation length of the surface lubricating portion and the less lubricious portion is preferably 100 mm to 1,000 mm, and more preferably 300 mm to 900 mm. According to this installation length, while operability is satisfactorily ensured when the catheter is inserted, more excellent backup capability can be achieved since the less lubricious portion more efficiently and more reliably comes into contact with the body lumen wall when the catheter indwells the body lumen.

The surface lubricating portion and the less lubricious portion are formed on the outer surface of the catheter at the same position in the axial direction of the catheter. Here, the "same position in the axial direction of the catheter" means that both the surface lubricating portion and the less lubricious portion are formed on a cross section at a certain position of the catheter. The position for forming the surface lubricating portion and the less lubricious portion on the outer surface of the catheter is not particularly limited as long as both of these are located at the same position in the axial direction of the catheter. The surface lubricating portion and the less lubricious portion positions vary depending on a shape of the catheter, an introducing position, an indwelling position, or the like. In FIG. 4, a half of the outer surface around the wire member is formed to be the deformable region, the less lubricious portion 25 is on the outer surface at the deformable region, and the surface lubricating portion 26 is formed on the remaining half of the outer surface of the catheter. However, the disclosure is not limited to coating half of the surface in this manner. Specifically, in a case where one wire member 24 is parallel to the lumen of the catheter main body 22 and extends in the axial direction, the less lubricious portion 25 is formed so that an angle ("θ" in FIG. 9) formed between an extension line (line "L" in FIG. 9) of a line connecting the center of the wire member 24 and an axis 28 of the catheter and a line connecting an end portion in the circumferential direction of the less lubricious portion 25 is preferably ±5° to ±90°, and more preferably ±15° to ±90°. In addition, in a case where multiple wire members 24 are parallel to the lumen of the catheter main body 22 and extend in the axial direction so as to be eccentric to the central axis (axis), the less lubricious portion 25 is formed so that an angle formed between the extension line of the line connecting a center point of two wire members farthest away from each other and the axis 28 of the catheter and the line connecting the end portion in the circumferential direction of the less lubricious portion 5 is preferably ±5° to ±90°, and more preferably ±15° to ±90°. If the less lubricious portion is formed in this state, backup capability (i.e., ability to indwell or retain the catheter in place) can be further improved. The surface lubricating portion 26 is formed so that an angle ("θ" in FIG. 9) formed between the line connecting the center of the wire member 24 and the axis 28 of the catheter and the line connecting the end portion in the circumferential direction of the surface lubricating portion 26 and the axis 28 of the catheter is preferably ±5° to ±90°, and more preferably ±15° to ±90°. When multiple wire members 24 are present, the above-described angle is also set to be an angle formed between the extension line of the line connecting the center point of two wire members farthest away from each other and the axis 28 of the catheter and the line connecting the end portion in the circumferential direction of the surface lubricating portion and the axis of the catheter. If the less lubricious portion is formed as described, operability can be further improved. Therefore, since the less lubricious portion and the surface lubricating portion are present in the same axial region the catheter can also be smoothly inserted into the vascular bent section, and the catheter can be more firmly held at a predetermined position inside the body lumen (for example, the blood vessel). In addition, the above-described angles θ and θ' may be the same size, or may be respectively different sizes.

The catheter main body 22 is configured to include a flexible and tubular member, and internally has the lumen 27 formed from the proximal end to the distal end. The lumen 27 is a lumen for a guide wire. A guide wire (not illustrated) is inserted into the lumen 27 when the catheter 21 is inserted into the blood vessel. In addition, the lumen 27 can allow the passage/injection of a drug solution, an embolus material, a contrast agent, or the like.

The hub 11 functions as an insertion port for inserting the guide wire into the lumen 27, and an injection port or the like for injecting the drug solution, the embolus material, the contrast agent, or the like into the lumen 27. The hub 11 also functions as a gripping portion when the catheter 21 is operated.

In addition, a catheter distal portion is a portion extending from the catheter main body, and can employ various known structures in the related art. For example, the distal portion may have a shape bent in a loop shape, or may have a substantially linear shape. In addition, a member for providing functions such as cleaning, aspirating, lighting, and imaging may be attached to the distal portion.

Although not particularly limited, the catheter main body (substrate tube (inner layer) 31 and outer layer 33) is normally a flexible material. Examples of materials for the catheter main body include polyolefin such as polypropylene, polyethylene, and ethylene-vinyl acetate copolymer, polyester such as polyamide (for example, nylon 11, nylon 12, and nylon 6), polyethylene terephthalate (PET), and polybutylene terephthalate (PBT), fluorine-based resins such as polyurethane, polyvinyl chloride, polystyrene-based resins, perfluoroalkoxy fluorine (PFA), polytetrafluoroethylene (PTFE), polyvinylidene fluoride, and ethylene-tetrafluoroethylene copolymer (ETFE), resins such as acrylonitrile-butadiene-styrene copolymer synthetic resins (ABS resin), and polyamide, various elastomers such as polyamide elastomer, polyester elastomer, polyurethane elastomer, polystyrene elastomer, fluorine-based elastomer, silicone rubber, and latex rubber, or a combination of two or more materials. Here, for example, a representative example of the polyamide elastomer includes a block copolymer in which various aliphatic or aromatic polyamides such as nylon 6, nylon 64, nylon 66, nylon 610, nylon 612, nylon 46, nylon 9, nylon 11, nylon 12, N-alkoxymethyl modified nylon, hexamethylenediamine-isophthalic acid condensation polymer, and metaxyloyl-diamine adipic acid condensation polymer are subjected to hard segments, and polymers such as polyester, and polyether, are subjected to soft segments. In addition, it is possible to use a polymer alloy (polymer blend) between polyamide and a very flexible resin, a graft copolymer, a random copolymer, those in which polyamide is softened using a plasticizer and the like, or a mixture of these materials. In addition, a representative example of the polyester elastomer includes a block copolymer between saturated polyester such as polyethylene terephthalate, and polybutylene terephthalate, and polyether or polyester. In addition, it is possible to use these polymer alloys, those in which saturated polyester is softened using the plasticizer and the like, or a mixture of these materials.

Among these materials, suitable strength can be preferably provided in the inner layer and the outer layer by using an ABS resin or a polyether-based polyamide resin. In addition, a fluorine-based resin or preferably PTFE is used for the inner layer. These materials allow improved operability of the guide wire or the catheter for treatment to be inserted into the lumen. The catheter is inserted while the position is confirmed under X-ray fluoroscopy. Accordingly, it is preferable to previously mix a material configuring the catheter main body with a radiopaque material such as barium sulfate, bismuth oxide, and tungsten. The radiopaque material makes it possible to easily confirm an insertion state, the position, or the like of the catheter under X-ray fluoroscopy. In addition, when the distal portion is configured to include the substrate tube (inner layer) and the outer layer, the inner layer and the outer layer can be bonded to each other using respectively suitable adhesives, or can be thermally fused to each other. Alternatively, both of these can be integrally molded by means of coating molding or the like. The outer layer may have a multilayer structure on which a further different resin is stacked.

In addition, a low friction layer may be formed on the inner surface of the catheter main body by using a low friction material, or the inner layer may be formed of the low friction material. The low friction material may be any material that reduces friction on the inner surface of the lumen. Examples of low friction materials polytetrafluoroethylene, a perfluoroalkoxy resin, polyethylene, polyimide, or the like. For example, the inner layer can be formed by using a dip coating method. In this case, an installation position of the low friction layer in the longitudinal direction of the catheter main body is not particularly limited. However, it is preferable to install the low friction layer over the entire length of the catheter main body. Alternatively, the catheter main body (substrate tube) may be configured to include a material used for the low friction layer. Sliding resistance against the guide wire inserted into the lumen is reduced by disposing the low friction layer in this way. Accordingly, it is possible to more easily and smoothly perform an operation for inserting the catheter into the blood vessel along the preceding guide wire or an operation for removing the guide wire from the catheter.

A reinforcement layer may be installed on the outer surface of the catheter. The reinforcement layer may be configured to include any desired material. For example, the reinforcement layer can include a braided body of a metal wire or a metal ribbon made of a steel wire or the like. It is also possible to use a coil formed of a hard material such as metal or a tube with slits for the reinforcement layer. The reinforcement layer may be disposed on the inner surface of the catheter, or may be embedded into the catheter. Here, the installation position of the reinforcement layer in the longitudinal direction of the catheter main body may be optionally determined. For example, the reinforcement layer may be installed over the entire length of the catheter main body, or the reinforcement layer may be installed at a location except for the distal portion of the catheter main body. Alternatively, the reinforcement layer may be arranged in a portion of the catheter main body. As described above, the installation position of the reinforcement layer can be appropriately changed depending on the purpose of using the catheter, required properties, or the like.

The material (or materials) of the reinforcement member (first reinforcement member and second reinforcement member) is not particularly limited, and a resin material or a metal material can be used. Here, the metal material is not limited to the following materials, but includes stainless steel, a nickel-titanium alloy, platinum, iridium, tungsten, and the like. Examples of the resin material include polyester such as polyethylene terephthalate and polybutylene terephthalate, polyolefin such as polyethylene and polypropylene, various thermoplastic resins such as polyvinyl chloride, polyamide, polyimide, polystyrene, thermoplastic polyurethane, polycarbonate, an ABS resin, an acrylic resin, polymethyl methacrylate (PMMA), polyacetal (PA), polyarylate, polyoxymethylene (POM), high tensile polyvinyl alcohol, a fluorine resin, polyvinylidene fluoride (PVdF), polytetrafluoroethylene, saponified ethylene vinyl acetate (EVOH), polysulfone, polyether sulfone, polyether ketone, polyphenylene oxide, and polyphenylene sulfide, various thermoplastic elastomers such as polyamide elastomer, polyester elastomer, polyurethane elastomers, and polyolefin elastomer, a polymer alloy containing any one of the above-described materials, or a combination of two or more materials. In a combination of two or more materials, it is preferable to select materials which are compatible with each other for both the reinforcement members (first reinforcement member and second reinforcement member). For example, a combination of the resin materials which are compatible with one another includes polyurethane and polyamide, polyamide and polyamide elastomer, polyethylene or polypropylene and polyolefin elastomer, polyethylene terephthalate and polyester elastomer, polyurethane and polyester elastomer, or high plasticity polyvinyl chloride and low plasticity polyvinyl chloride, and the like. The first reinforcement member and the second reinforcement member may be configured to include the same material, or may be configured to include respectively different materials.

The reinforcement member (first reinforcement member and second reinforcement member) may be a single fiber, or may be a fiber assembly obtained by weaving the single fiber.

A cross-sectional shape of the reinforcement member (first reinforcement member and second reinforcement member) is not particularly limited, and may have any desired shape such as a circular shape, and a flat shape (ribbon shape, belt shape). The respective cross-sectional shapes of the first reinforcement member and the second reinforcement member may be the same or may be different from each other.

The thickness of the reinforcement member (first reinforcement member and second reinforcement member) is not particularly limited. For example, when the reinforcement member has a circular cross-sectional shape, the diameter is preferably approximately 0.01 mm to 0.5 mm, and more preferably approximately 0.03 mm to 0.3 mm. When the reinforcement member has a ribbon cross-sectional shape, the reinforcement member preferably has the width of approximately 0.03 mm to 5 mm, and the thickness of approximately 0.03 mm to 0.2 mm. The configuration of the reinforcement member allows sufficient reinforcing effect to be obtained despite a relatively thin thickness. Accordingly, the diameter of the catheter is advantageously reduced. Sizes of the reinforcement member and a rigid portion may be the same or may be different from each other. In addition, the diameter or the width of the reinforcement member (first reinforcement member and second reinforcement member) may not be constant over the entire length of the catheter main body, and may be continuously or intermittently changed. For example, the diameter or the width of one reinforcement member (first reinforcement member or second reinforcement member) may decrease from the proximal side toward the distal side of the catheter main body, and the diameter or the width of the other reinforcement member (second reinforcement member or first reinforcement member) may increase from the proximal side toward the distal side of the catheter main body. In this manner, density of both the reinforcement members may be further changed.

Although not particularly limited, the wire member can include at least either a metal member or a non-metal member. For example, it is possible to use a material having the metal member formed in a helical shape, a material having the non-metal member formed in a helical shape, a material having the metal member and the non-metal member which are superimposed on each other and formed in a helical shape or the like. For example, the metal member material can be one of, or a combination of two or more of, stainless steel, a nickel-titanium alloy, platinum, iridium, tungsten, and the like. The non-metal member material can be one of, or a combination of two or more of, carbon, polyamide, polyethylene terephthalate, polybutylene terephthalate, and the like. It is preferable to configure the reinforcement member and the wire member so as to include a radiopaque material such as tungsten, platinum, iridium, and an alloy containing these materials. The radiopaque material allows the catheter to be satisfactorily visible under X-ray fluoroscopy. In addition, elasticity in the axial direction of the catheter can be more easily controlled. The wire member may be configured to include the same material as that of the reinforcement member, or may be configured to include a material different from that of the reinforcement member.

A cross-sectional shape of the wire member is not particularly limited, and may have any desired shape such as a circular shape, and a flat shape (ribbon shape, belt shape). The cross-sectional shape of the wire member may be the same as that of the reinforcement member, or may be different.

The wire member thickness is not particularly limited. For example, when the wire member has a circular cross-sectional shape, the diameter is preferably approximately 10 µm to 100 µm, and more preferably approximately 30 µm to 60 µm. In addition, when the wire member has a ribbon cross-sectional shape, the wire member preferably has the width of approximately 0.1 mm to 1.0 mm, and the thickness of approximately 0.04 mm to 0.05 mm. Elasticity of the catheter can be easily controlled by arranging the wire member in this way. In addition, the diameter of the catheter is advantageously reduced. The thickness of the wire member may be the same as the thickness of the reinforcement member, or may be different.

As described above, at least a portion of the outer surface of the catheter main body is covered with the surface lubricating portion and the less lubricious portion at the same position in the axial direction. Here, the thickness of the surface lubricating portion is not particularly limited as long as sufficient lubricity can be obtained. However, it is preferable that the surface lubricating portion has the thickness which enables the surface lubricating portion to be firmly fixed to the catheter substrate to achieve excellent surface lubricity and durability (lubricity maintainability) when in use. The thickness of the surface lubricating portion (thickness of the lubricating portion when not swollen) is preferably within a range of 0.1 µm to 20 µm, more preferably 0.5 µm to 10 µm, and most preferably 1 µm to 5 µm. According to this thickness, a uniform film can be easily formed, and surface lubricity and water retention (lubricity maintainability) can be sufficiently achieved.

A material for configuring the surface lubricating portion may employ any material as long as the material absorbs water to show lubricity. For example, the material includes a hydrophilic material. The following materials represent specific examples.

For example, the hydrophilic material configuring the surface lubricating portion includes cellulose-based polymer materials such as polyvinyl pyrrolidone, polyvinyl alcohol, polyethylene oxide-based polymer materials, and carboxymethyl cellulose, acrylamide-based polymer materials such as polyacrylamide, and polydimethyl acrylamide, maleic anhydride-based polymer materials such as hyaluronic acid, polyacrylic acid, and maleic anhydride-methyl vinyl ether copolymer, water-soluble Nylon (registered trademark), or hydrophilic polymers such as derivatives of the materials. According to these hydrophilic polymers, lubricity can be provided by absorbing water when the catheter is wet. In order to firmly fix these hydrophilic polymers to the catheter (catheter substrate), it is preferable to prepare the crosslinking of the hydrophilic polymers by adding a suitable amount of crosslinking agent or by introducing a reactive functional group to the hydrophilic polymers for forming the surface lubricating portion, for example.

A method of introducing the reactive functional group to the hydrophilic polymers includes a method of copolymerizing a monomer having the reactive functional group (hereinafter, referred to as a "reactive monomer") and a hydrophilic monomer. Here, the reactive monomer means a monomer having the reactive functional group which enables crosslinking reaction or the like. In the present description, the "reactive functional group" indicates a functional group which enables crosslinking reaction with other monomers or reaction (coupling) with the catheter substrate by means of thermal processing, light emitting, electron beam emitting, radiation exposure, plasma emitting, or the like.

The reactive functional group is not particularly limited, but can include a functional group such as an epoxy group, an acid halide group, an aldehyde group, an isocyanate group, and an acid anhydride group. Among these groups, from a viewpoint of handling convenience, crosslinking reaction efficiency, or the like, as a monomer having the reactive functional group (reactive monomer), it is preferable to use a monomer having the epoxy group, the isocyanate group, or the aldehyde group. It is particularly preferable to use a monomer having the epoxy group. These reactive functional groups may be present alone in the reactive monomer, or may be present at multiple locations.

It is preferable that the reactive monomer used in the disclosed catheter has the reactive functional group, and that in a body fluid or in an aqueous solvent, hydrophobicity is further provided than the hydrophilic monomer used when at least a copolymer is manufactured. Specifically, the reactive monomers can include a monomer having an epoxy group such as glycidyl acrylate, glycidyl methacrylate (GMA), methyl glycidyl methacrylate, and allyl glycidyl ether in the molecule; a monomer having an acid halide group such as (meth)acrylic acid chloride, (meth)acrylic acid bromide, and (meth)iodide acrylic acid in the molecule; a monomer having an aldehyde group such as (meth)acryl aldehyde, crotonaldehyde, acrolein, and methacrolein in the molecule; a monomer having an isocyanate group such as (meth)acryloyloxy methyl isocyanate, (meth)acryloyloxyethyl isocyanate, (meth)acryloyloxy propyl isocyanate, and (meth)acryloyl isocyanate in the molecule; a monomer having an acid anhydride group such as maleic anhydride, itaconic anhydride, and citraconic anhydride in the molecule; or like. Among these materials, as the monomer having the reactive functional group, it is preferable to use a monomer having the epoxy group. It is more preferable to use glycidyl acrylate or glycidyl methacrylate in which reaction is accelerated by heat or the like, and in which handling is relatively easy. The reactive monomers can be used alone or in a combination of two or more types.

In addition, although not particularly limited, for example, the hydrophilic monomer can include acrylamide and derivatives thereof, vinyl pyrrolidone, acrylic acid and methacrylic acid and derivatives thereof, polyethylene glycol acrylate and derivatives thereof, a monomer having sugar or phospholipid in the side chain, or a water-soluble monomer such as maleic anhydride. More specifically, the hydrophilic monomer includes acrylic acid, methacrylic acid, N-methyl acrylamide, N,N'-dimethylacrylamide, acrylamide, acryloyl morpholine, N,N'-dimethylaminoethyl acrylate, vinyl pyrrolidone, 2-methacryloyloxyethyl phosphorylcholine, 2-methacryloyloxyethyl-D-glycoside, 2-methacryloyloxyethyl-D-mannoside, vinyl methyl ether, 2-hydroxyethyl (meth)acrylate, 4-hydroxybutyl (meth)acrylate, 2-hydroxypropyl (meth)acrylate, 2-hydroxybutyl (meth)acrylate, 6-hydroxyhexyl (meth)acrylate, 1,4-cyclohexanedimethanol mono (meth)acrylate, 1-chloro-2-hydroxypropyl (meth)acrylate, diethylene glycol mono (meth)acrylate, 1,6-hexanediol mono (meth)acrylate, pentaerythritol tri (meth)acrylate, dipentaerythritol penta (meth)acrylate, neopentyl glycol mono (meth)acrylate, trimethylolpropane di (meth)acrylate, trimethylethane di (meth)acrylate, 2-hydroxy-3-phenyloxy-propyl (meth)acrylate, 4-hydroxycyclohexyl (meth)acrylate, 2-hydroxy-3-phenyl-oxy (meth)acrylate, 4-hydroxycyclohexyl (meth)acrylate, cyclohexanedimethanol mono (meth)acrylate, poly (ethylene glycol) methyl ether acrylate, and poly (ethylene glycol) methyl ether methacrylate. From a viewpoint of easy synthesis and operability, it is preferable to use N,N-dimethylacrylamide, acrylamide, acrylic acid, methacrylic acid, N,N-dimethylaminoethyl acrylate, 2-hydroxyethyl methacrylate, and vinyl pyrrolidone. It is more preferable to use N,N'-dimethylacrylamide, and N,N'-dimethylaminoethyl acrylate. It is particularly preferable to use N,N'-dimethylacrylamide. The hydrophilic monomers can be used alone or in a combination of two or more types.

In order to provide satisfactory lubricity, the hydrophilic polymer is preferably a copolymer of the reactive monomer and the hydrophilic monomer, and more preferably a block copolymer of a block formed of a monomer having the reactive functional group and a block formed of the hydrophilic monomer (block copolymer of the reactive monomer and the hydrophilic monomer). If the hydrophilic polymer is the block copolymer, satisfactory strength or lubricity of the surface lubricating portion can be obtained.

In addition, according to the more preferable embodiment of the disclosed catheter, the hydrophilic polymer is a block copolymer which has a reactive domain in which the monomer having the epoxy group serves as at least one structural unit, and a hydrophilic domain in which the hydrophilic monomer serves as at least one structural unit. The epoxy group which is the reactive functional group reacts with the neighboring epoxy group in addition to the reaction with the catheter base, thereby causing the neighboring hydrophilic polymer to form a crosslinking structure. Accordingly, strength of the surface lubricating portion can be improved.

A ratio between the hydrophilic monomer and the reactive monomer in the hydrophilic polymer is not particularly limited. In view of satisfactory lubricity, film strength, bonding strength to firmly adhere to the catheter substrate, or the like, a molar ratio between the hydrophilic monomer and the reactive monomer is preferably 1:1 to 100:1, more preferably 5:1 to 80:1, and most preferably 10:1 to 50:1. According to this ratio, the ratio between a hydrophilic area and a reactive area of the hydrophilic polymer can fall within a satisfactory range. If the ratio falls within this range, the surface lubricating portion can be sufficiently provided with improved lubricity by the hydrophilic area, and can be provided with improved durability (lubricity maintainability) and film strength by the reactive area.

Without being particularly limited, as a manufacturing method (polymerizing method) of the hydrophilic polymer for polymerizing the hydrophilic polymer, a known polymerizing method can be used. However, in general, a monomer may be polymerized by using a polymerization initiator. In addition, in a case where the hydrophilic polymer according to the present invention is a block copolymer or a graft copolymer, for example, the polymerizing method can include living polymerization, polymerization using a macromonomer, polymerization using a polymerization initiator for polymer, polycondensation, or the like. However, the polymerizing method is not particularly limited.

As the hydrophilic polymer (surface lubricating portion) of the catheter disclosed here, it is preferable to use a maleic anhydride-methyl vinyl ether copolymer, or a glycidyl methacrylate-dimethylacrylamide copolymer, and more preferable to use the glycidyl methacrylate-dimethylacrylamide copolymer (particularly, a block copolymer).

The above-described hydrophilic material is provided with lubricity by being wet (absorbing water), thereby reducing frictional resistance between the catheter and the inner wall of the body lumen. These hydrophilic materials cover the catheter so as to be fixed as the surface lubricating portion by using a known technique in the related art such as dip coating, spray coating, and surface graft polymerization.

[Manufacturing Method of Catheter]

A manufacturing method of the catheter according to the present invention is not particularly limited. A known method is applicable in a similar manner or in a suitably modified manner. For example, after the catheter outer periphery (outer surface) is covered with the surface lubricating layer formed of the hydrophilic material, the less lubricious portion having decreased lubricity can be formed by selectively emitting an energy beam to the deformable region configured to be located on the inner side when the catheter is bent. The presence of this less lubricious portion increases the friction coefficient (decreases lubricity) when the catheter comes into contact with the body lumen wall. Therefore, it is possible to provide the catheter which has excellent operability and indwelling convenience while satisfactory backup capability (i.e., ability to be held firmly in place) is ensured.

That is, according to a preferred embodiment of the manufacturing method of the catheter in the present invention, after the surface lubricating portion is formed on the catheter surface (i), the less lubricious portion is formed by emitting the energy beam to at least a portion of the obtained surface lubricating portion (ii). Hereinafter, a preferred manufacturing method (method of forming the surface lubricating portion and the less lubricious portion) of the catheter according to the present invention will be described. However, method of manufacturing the catheter disclosed here is not limited to the following method.

(Process (i))

In this process, the surface lubricating portion is formed on the catheter surface.

The catheter may be manufactured by using any desired method before forming the surface lubricating portion and the less lubricious portion. A known manufacturing method is applicable in a similar manner or in a suitably modified manner. For example, in a case where the catheter has the coil-shaped reinforcement member and the wire member, polytetrafluoroethylene is used for a material of the inner layer, and is subjected to extrusion molding on a core material, thereby preparing an inner layer tube. Then, polyester is used for a material of the outer layer, and a tungsten wire (reinforcement member) having a suitable size (for example, width of 40 μm and thickness of 15 μm) is wound around the outer surface of the inner layer tube, while a wire member configured to include stainless steel (material) having a suitable size (for example, width of 15 μm and thickness 15 μm) is braided in the longitudinal direction, thereby obtaining an intermediate structure body. Thereafter, the intermediate structure body is covered with the outer layer tube prepared by using polyester for the material of the outer layer, and the inner layer tube and the outer layer tube are bonded to each other. In this manner, it is possible to obtain the catheter main body (for example, outer diameter of 0.90 mm and inner diameter of 0.50 mm) having a penetrating lumen (i.e., a through lumen).

Next, the surface lubricating portion is formed on the catheter surface manufactured as described above. Here, a material for configuring the surface lubricating portion is as described above. In addition, the process (i) is not particularly limited except that the above-described hydrophilic material is used. A known method is applicable in a similar manner or in a suitably modified manner.

Specifically, the manufacturing method includes forming the surface lubricating portion in such a way that the above-described hydrophilic polymer (particularly, a block copolymer is preferred) is dissolved in a solvent to prepare a coating solution (lubricant coating agent or a coating solution). After a coating layer is formed by coating the catheter substrate with the coating solution, the coating layer is thermally processed, and the hydrophilic polymer (block copolymer) is subjected to crosslinking reaction. It is preferable that the method of forming the surface lubricating portion includes at least a coating process of coating the catheter substrate with a lubricant coating agent and a heating process of performing thermal processing on the lubricant coating agent coating layer. This method can provide the catheter surface with satisfactory lubricity and durability.

In the above-described method, a solvent used in dissolving the hydrophilic polymer is not particularly limited as long as the hydrophilic polymer can be dissolved. Specifically, the solvent can include water, alcohols such as methanol, ethanol, isopropanol, and ethylene glycol, ketones such as acetone, and methyl ethyl ketone, esters such as ethyl acetate, halides such as chloroform, olefins such as hexane, ethers such as tetrahydrofuran, and butyl ether, aromatics such as benzene, and toluene, amides such as N,N-dimethylformamide (DMF). However, the solvent is not limited to these materials. These materials may be used alone, or two or more of the materials may be used in combination.

The concentration of the hydrophilic polymer contained in the coating solution is not particularly limited. For improved coating performance, availability of a desired effect (lubricity and durability), and the like, the concentration of the hydrophilic polymer contained in the coating solution is 0.01 wt % to 20 wt %, more preferably 0.05 wt % to 15 wt %, and most preferably 0.1 wt % to 10 wt %. If the concentration of the hydrophilic polymer falls within the above-described range, the obtainable surface lubricating portion can be sufficiently provided with lubricity and durability. In addition, it is possible to easily obtain the surface lubricating portion which has a desired uniform thickness by performing coating once. Accordingly, it is preferable that the concentration falls within the range in terms of operability (for example, coating convenience) and production efficiency. However, even if the concentration is beyond the above-described range, as long as the range does not affect an operation effect of the present invention, the concentration can be acceptably utilized.

As a method of coating the catheter substrate surface with the coating solution, without being particularly limited, a known method in the related art is applicable such as a coating and printing method, a dipping method (dipping method and dip coating method), an atomizing method (spraying method), a spin coating method, and a mixed solution impregnation sponge coating method. Among these methods, it is preferable to use the dipping method (dipping method and dip coating method). When the surface lubricating portion is also formed on a thin and narrow inner surface of the catheter, the catheter (catheter substrate) may be dipped into the coating solution, and the system may be internally decompressed so as to remove gas. Decompressing and removing gas causes the solution to quickly permeate the thin and narrow inner surface. Accordingly, it is possible to facilitate the formation of the surface lubricating portion.

When the surface lubricating portion is formed on only a portion of the catheter, only the portion of the catheter (catheter substrate) is dipped into the coating solution and that portion of the catheter (catheter substrate) is coated with the coating solution. The surface lubricating portion can thus be formed in a desired surface portion of the catheter (catheter substrate).

When it is difficult to dip only a portion of the catheter into the coating solution, a catheter surface portion that is not desired to form the surface lubricating portion is protected in advance by (for example, covered with) a suitable member or a material which is removable (detachable). Then, the catheter is dipped into the coating solution, and the catheter is coated with the coating solution. Thereafter, the protecting member (material) is detached from the catheter surface portion. Thermal processing is then performed for reaction, thereby enabling the surface lubricating portion to be formed on the desired surface portion of the catheter. However, according to the disclosed manufacturing methods, without being limited to these forming methods, the surface lubricating portion can be formed by appropriately utilizing a known method in the related art. For example, when it is difficult to dip only the portion of the catheter into the mixed solution, instead of the dipping method, other coating techniques may be applied (for example, a predetermined surface portion of a medical device is coated with a coating solution by using a coating device such as a spray device, a bar coater, a die coater, a reverse coater, a comma coater, a gravure coater, a spray coater, and a doctor knife). When it is necessary to form the surface lubricating portion on both the outer surface and the inner surface of the catheter, the dipping method is preferably used so that both the outer surface and the inner surface can be coated at the same time.

After the catheter is dipped into the coating solution containing the hydrophilic polymer, the catheter is removed from the coating solution to perform thermal processing. Conditions for performing thermal processing on the coating solution (temperature, time, or the like) are not particularly limited as long as the surface lubricating portion containing the hydrophilic polymer can be formed on the catheter. Specifically, heating temperature is preferably 60° C. to 200° C., more preferably 80° C. to 160° C., much more preferably higher than 80° C. and equal to or lower than 150° C., and particularly preferably 90° C. to 140° C. In addition, a heating period of time is preferably 15 minutes to 24 hours, and preferably 1 hour to 10 hours. According to these conditions, crosslinking reaction is caused by the reactive functional group of the hydrophilic polymer. It is thus possible to form a strong surface lubricating portion which is not easily separated from the catheter.

When the reactive functional group contained in the hydrophilic polymer employs an epoxy group, the epoxy group is subjected to self-crosslinking through heating. However, in order to promote crosslinking reaction, an epoxy reaction catalyst or a multifunctional crosslinking agent which can react with the epoxy group may be contained in the coating solution.

In addition, the pressure conditions during thermal processing are not limited. The thermal processing can be performed under normal pressure (atmospheric pressure), and may be performed under increased pressure or decreased pressure.

For example, it is possible to use an oven, a vacuum dryer, or the like as the thermal processing means or thermal processing device.

According to the above-described method, after the film (coating layer) of the hydrophilic polymer is formed on the substrate surface, the reactive functional group is subjected to crosslinking. In this manner, it is possible to form a first surface lubricating portion which is strong and is not easily separated from the substrate. Therefore, the catheter disclosed here can be manufactured with excellent lubricity and durability properties.

(Process (ii))

In this process, an energy beam is emitted to at least a portion of the surface lubricating portion formed in the above-described process (i), thereby forming the less lubricious portion. The energy beam is emitted to the surface lubricating portion to decrease the lubricity. Here, although the particular mechanism by which the lubricity of the emitted portion is decreased by emitting the energy beam is not fully known or understood, it is presumed as follows. The manufacturing method disclosed here is not limited to the following mechanism. That is, in a case where the hydrophilic polymer is a copolymer of a reactive monomer and a hydrophilic monomer, a hydrophilic area acts to provide lubricity in a body fluid or an aqueous solvent. On the other hand, if the energy beam is emitted to the copolymer, an active point is generated in the hydrophilic area. Crosslinking reaction occurs starting from the active point, thereby increasing crosslinking density of the surface lubricating portion (swelling degree of the surface lubricating portion decreases). Therefore, the hydrophilic area of the surface lubricating portion decreases to form the less lubricious portion.

The process of emitting the energy beam is not particularly limited as long as a form is used to obtain a uniform amount of the energy beam emitted to the catheter surface. It is possible to use a known method. When lubricity (i.e., the friction coefficient) is intended to be continuously and gradually changed, an emission amount of the energy beam may be gradually changed to control the lubricity (friction coefficient). However, from a viewpoint of ensuring operability (controllability of a beam source) and backup capability, it is preferable to uniformly emit the energy beam.

In addition, to improve emission efficiency of the energy beam and achieve uniform emission, the energy beam generated by the beam source may be emitted to the first surface lubricating portion after the energy beam emitted from the generating source is reflected on a reflection plate. The energy beam emission is applicable to not only a batch process but also a continuous process.

As long as the energy beam can modify the surface of the surface lubricating portion and can decrease the lubricity (increase the friction coefficient) in the surface lubricating portion, any beam may be used. However, specifically, the energy beam can include an ultraviolet beam, a γ ray, an electron beam, and the like. Among these beams, it is preferable to use the ultraviolet beam to easily control the emission amount and the emission range. If the ultraviolet beam is used as the energy beam, the friction coefficient can increase approximately 3 times to 50 times in a region to which the ultraviolet beam is emitted, compared to a region to which the ultraviolet beam is not emitted.

The below description describes the emission conditions when the ultraviolet beam is used as the energy beam in more detail.

In the present description, the "ultraviolet beam" generally indicates an electromagnetic wave having a wavelength of 10 nm to 400 nm. Although not particularly limited, it is possible to use a low pressure mercury lamp (wavelength: 254 nm), a high pressure mercury lamp (wavelength: 365 nm), a deuterium lamp (wavelength: 185 nm to 400 nm), a xenon excimer lamp (wavelength: 172 nm), a metal halide lamp (wavelength: 200 nm to 450 nm), and the like as the beam source of the ultraviolet beam. A fluorescent lamp, a yellow lamp, or the like may also be used. Among these lamps, it is preferable to use a mercury lamp, such as the low pressure mercury lamp and the high pressure mercury lamp.

The emission conditions of the energy beam are not particularly limited. However, it is preferable to select a condition under which the less lubricious portion having the above-described friction coefficient can be formed. The friction coefficient (reduced degree of surface lubricity) of the less lubricious portion can be appropriately controlled by controlling a type of energy beams to be used, a wavelength, an emission period of time, or the like.

Illuminance of the ultraviolet beam is not particularly limited. However, it is preferable that the illuminance is 1 mW/cm$^2$ to 1,000 mW/cm$^2$. In addition, emission energy is not particularly limited. However, it is preferable that the emission energy is 100 mJ/cm$^2$ to 20,0000 mJ/cm$^2$. The less lubricious portion having the above-described friction coefficient can be formed by setting the conditions within these ranges.

Although not particularly limited, a period of time for emitting the ultraviolet beam is appropriately selected depending on a type of hydrophilic materials for forming the surface lubricating portion. Usually, the emission time is preferably 1 second to 30 minutes, more preferably 10 seconds to 20 minutes, much more preferably 1 minute to 15 minutes, and particularly preferably 3 minutes to 10 minutes.

In addition, an emission atmosphere of the ultraviolet beam may be either an air atmosphere or an inert gas atmosphere.

The above-described emission conditions enable forming a high lubricity region and a low lubricity region on the surface lubricating portion formed of the same material.

The device can selectively emit the energy beam to a predetermined position of the surface lubricating portion by emitting a thin and focused energy beam. The energy beam can also be emitted to only a portion of the surface lubricating layer by successively moving the catheter or the energy beam. Alternatively, the energy beam may be emitted to the catheter in a wide range. In this case, the surface lubricating portion may be protected by (covered with) another member (material) so that the energy beam is emitted to a portion of the surface lubricating portion and the energy beam is not emitted to the other portion. For example, a portion other than the less lubricious portion may be covered with a mask before the energy beam is emitted to the catheter.

In this manner, it is possible to easily manufacture the catheter having the less lubricious portion disposed at a desired position. When the obtained catheter indwells at a position inside a desired body lumen (for example, blood vessel), the less lubricious portion comes into contact with a body lumen wall. The friction force between the less lubricious portion of the catheter and the body lumen wall enables the catheter to be firmly held at the unchanged position (i.e., the catheter has excellent backup capability and is thus configured to be retained in place). The catheter can also be smoothly inserted into the body lumen because the surface lubricating portion for covering the outer surface other than the less lubricious portion is present. Therefore, the catheter according to the present invention is used to enable the catheter to have improved indwelling convenience at the desired position while operability is satisfactorily ensured when the catheter is introduced into the desired position.

An advantageous effect of the disclosed catheter will be described with reference to the following example and comparative example. However, the technical scope of the catheter is not limited to the following example. Unless otherwise described in the following example, an operation is performed at room temperature (25° C.). In addition, unless otherwise described, "%" and a "part" respectively mean "wt %" and a "part by weight".

Example 1

A polyamide elastomer (Grilamid ELG5660 made by EMS-Chemie Japan Ltd., shore hardness D62, hard segment: Nylon 12, soft segment: polytetramethylene glycol, soft segment content in an elastomer: 27 wt %; both terminals of the elastomer are not sealed) was subjected to press molding so as to obtain a sheet of 1 mm in thickness.

Separately, a DMF solution (1) was prepared in such a way that a block copolymer (DMMA:GMA (molar ratio)=12:1) having N,N-dimethyl acrylamide (DMAA) as a hydrophilic monomer and glycidyl methacrylate (GMA) as a reactive monomer is dissolved in a proportion of 5 wt %. Similarly, a DMF solution (2) was prepared in such a way that a block copolymer (DMMA:GMA (molar ratio)=38:1) having N,N-dimethyl acrylamide (DMAA) as the hydrophilic monomer and glycidyl methacrylate (GMA) as the reactive monomer is dissolved in a proportion of 5 wt %.

The prepared sheets were cut into 1.5 cm×5 cm, and were respectively dipped into the DMF solutions (1) and (2). The sheets were then subjected to thermal processing at 130° C. for 3 hours, thereby preparing the sheets (1) and (2) on which a surface lubricating layer having a thickness (thickness when not swollen) of 3 µm was formed on a surface thereof.

Next, an ultraviolet beam (wavelength: 254 nm, illuminance: 16 mW/cm$^2$) was emitted to the surface lubricating layer of the sheets (1) and (2) by using an ultraviolet emitting device PL16-110 made by Sen Engineering Co., Ltd.

Figure 11:
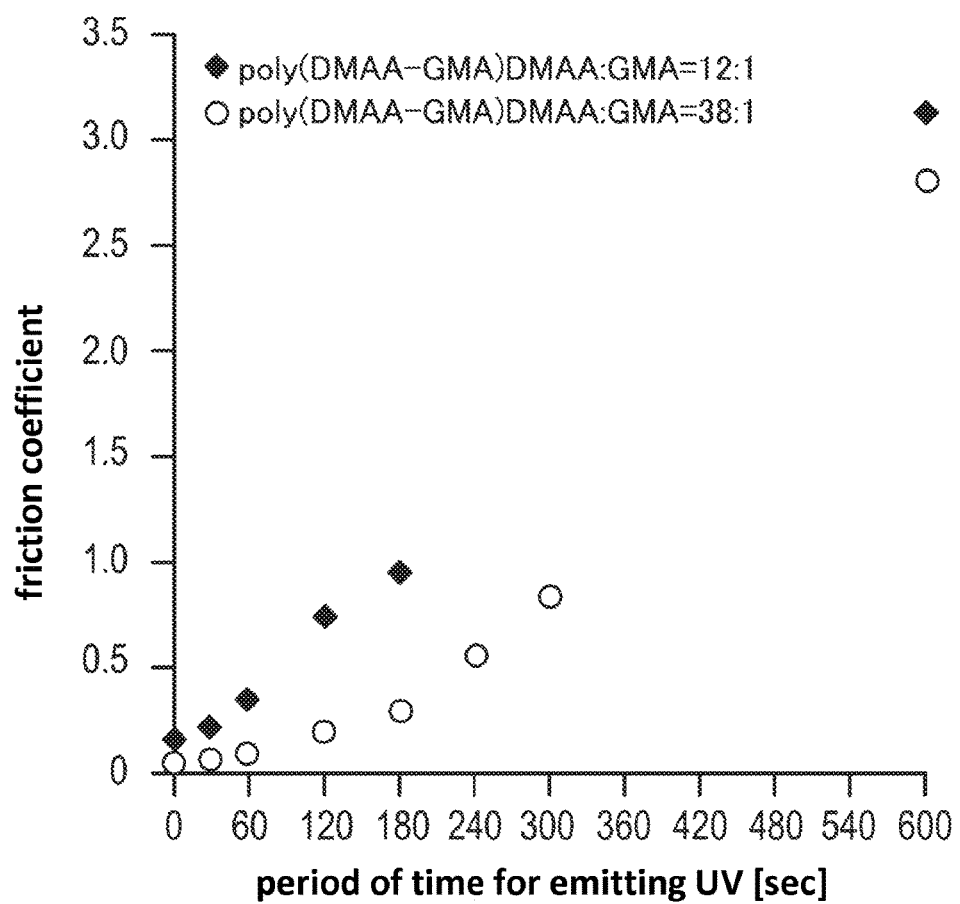
FIG. 11 is a graph illustrating lubricity evaluation test results of the less lubricious portion depending on an ultraviolet light irradiation period of time according to a first example.

The friction coefficient was evaluated by using the obtained sheets in this manner as a sample, in accordance with the above-described measurement method of the friction coefficient. FIG. 11 illustrates a relationship between a period of time for emitting the ultraviolet beam and the friction coefficient of the obtained samples. Based on the results in FIG. 11, it is understood that lubricity of the surface lubricating layer decreases in response to the period of time for emitting the ultraviolet beam, even if any coating agent is used, and that the lubricity of the surface can be optionally controlled.

The detailed description above describes embodiments of a catheter and operational method representing examples of the inventive catheter and operation disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter configured to be introduced into and indwelled in a body lumen, the catheter comprising:
   a lumen extending in an axial direction;
   a deformable region extending parallel to the lumen of the catheter;
   the catheter being bendable and possessing a curved section when being bent, the curved section possessing an inner side;

the deformable region being located on the inner side of the curved section when the catheter is bent to form the curved section;

a portion of an outer surface of the catheter being covered with a surface lubricating layer;

the outer surface of the deformable region including a less lubricious portion, the less lubricious portion being less lubricious than the surface lubricating layer on the portion of the outer surface of the catheter; and the portion of the outer surface of the catheter covered with the surface lubricating layer and the less lubricious portion of the deformable region being at the same axial position in the axial direction of the catheter.

2. The catheter according to claim 1, wherein the deformable region is less stretchable or is more contractible in a circumferential direction of the catheter than a region of the catheter having the surface lubricating layer on the outer surface.

3. The catheter according to claim 1, further comprising:
a reinforcement member possessing a coil shape;
a wire member extending parallel to the axial direction of the catheter; and
wherein the wire member is arranged on the same side of the catheter as the deformable region such that the wire member extends along the inner side of the curved section when the catheter is bent.

4. The catheter according to claim 1, further comprising:
a mesh reinforcement member;
a wire member extending parallel to the axial direction of the catheter;
wherein the lumen possesses a longitudinal axis; and
wherein the wire member is arranged on a side opposite to the deformable region with respect to the longitudinal axis of the lumen of the catheter such that the wire member extends along an outer side of the curved section when the catheter is bent.

5. The catheter according to claim 3, wherein the wire member is braided into the reinforcement member.

6. The catheter according to claim 4, wherein the wire member is braided into the mesh reinforcement member.

7. The catheter according to claim 1, wherein the less lubricious portion possesses a friction coefficient of 0.3 to 4.

8. The catheter according to claim 7, wherein the portion of the outer surface covered with the surface lubricating layer possesses a friction coefficient of 0.03 to 0.2.

9. A catheter comprising:
a lumen extending in an axial direction, the lumen possessing a longitudinal axis;
a main body possessing an outer surface and an outer circumference;
a reinforcement member embedded in the main body of the catheter and extending in the axial direction, the reinforcement member being coaxial with the longitudinal axis of the lumen;
a wire member embedded in the main body of the catheter and extending in the axial direction, the wire member possessing a longitudinal axis offset from the longitudinal axis of the lumen;
the main body of the catheter including a deformable region extending parallel to the lumen of the catheter in the axial direction and an other region opposite to the deformable region around the outer circumference;
the outer surface of the other region of the main body being covered with a surface lubricating layer, the outer surface of the deformable region being relatively less lubricious than the outer surface of the other region;
the catheter being bendable and possessing a curved section when bent, the curved section possessing an inner side and an outer side; and
the deformable region of the main body being located on the inner side of the curved section when the catheter is bent, and the other region of the main body being located on the outer side of the curved section when the catheter is bent.

10. The catheter according to claim 9, wherein
the reinforcement member possesses a helical shape, and
the wire member is embedded in the main body at the deformable region.

11. The catheter according to claim 9, wherein
the reinforcement member is a braided reinforcement member, and
the wire member is embedded in the main body at the other region.

12. The catheter according to claim 10, wherein the helically-shaped reinforcement member possesses a winding pitch that gradually changes from a proximal side to a distal side in the axial direction of the reinforcement member.

13. The catheter according to claim 9, wherein the wire member is a first wire member, and further comprising a second wire member embedded in the main body of the catheter and extending in the axial direction.

* * * * *